US009127089B2

(12) United States Patent
Ueno et al.

(10) Patent No.: US 9,127,089 B2
(45) Date of Patent: Sep. 8, 2015

(54) HIGHLY-PURIFIED SOLUBLE THROMBOMODULIN AND METHOD FOR PRODUCING SAME

(75) Inventors: Yuji Ueno, Tokyo (JP); Hiroki Shigematsu, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 13/641,047

(22) PCT Filed: Apr. 28, 2011

(86) PCT No.: PCT/JP2011/060348
§ 371 (c)(1),
(2), (4) Date: Dec. 21, 2012

(87) PCT Pub. No.: WO2011/136313
PCT Pub. Date: Nov. 3, 2011

(65) Prior Publication Data
US 2013/0143790 A1    Jun. 6, 2013

(30) Foreign Application Priority Data

Apr. 30, 2010 (JP) .................................. 2010-105421

(51) Int. Cl.
C07K 14/745 (2006.01)
A61K 38/00 (2006.01)

(52) U.S. Cl.
CPC ............. *C07K 14/7455* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,043,425 A | 8/1991 | Aoki et al. | |
| 5,202,421 A | 4/1993 | Kunihiro et al. | |
| 5,300,490 A | 4/1994 | Kunihiro et al. | |
| 5,378,816 A | 1/1995 | Pungor et al. | |
| 5,466,668 A | 11/1995 | Glaser et al. | |
| 5,516,659 A | 5/1996 | Nii et al. | |
| 5,574,007 A | 11/1996 | Zushi et al. | |
| 5,695,964 A | 12/1997 | Nii et al. | |
| 5,753,123 A | 5/1998 | Kajihara et al. | |
| 5,827,824 A | 10/1998 | Light et al. | |
| 5,834,028 A | 11/1998 | Kunihiro et al. | |
| 6,034,060 A | 3/2000 | Yamamoto et al. | |
| 6,063,763 A | 5/2000 | Light et al. | |
| 2004/0072314 A1 | 4/2004 | Champluvier et al. | |
| 2004/0102615 A1 | 5/2004 | Berna et al. | |
| 2007/0066806 A1 | 3/2007 | Coffman et al. | |
| 2010/0145020 A1* | 6/2010 | Ohigashi ...................... 530/381 |
| 2010/0305305 A1 | 12/2010 | Poulle et al. | |
| 2013/0237693 A1 | 9/2013 | Ohigashi | |

FOREIGN PATENT DOCUMENTS

| | | |
|---|---|---|
| CA | 2 681 294 A1 | 10/2008 |
| CN | 1151406 A | 6/1997 |
| CN | 101641368 A | 2/2010 |
| EP | 0312598 A1 | 4/1989 |
| EP | 0356836 A2 | 3/1990 |
| EP | 0376251 A2 | 7/1990 |
| EP | 0412841 A1 | 2/1991 |
| EP | 0445681 A2 | 9/1991 |
| EP | 0474273 A2 | 3/1992 |
| EP | 0489180 A1 | 6/1992 |
| EP | 0689843 A1 | 1/1996 |
| EP | 0770626 A2 | 5/1997 |
| EP | 2 138 505 A1 | 12/2009 |
| JP | 64-6219 A | 1/1989 |
| JP | 2-256699 A | 10/1990 |
| JP | 3-86900 A | 4/1991 |
| JP | 3-133380 A | 6/1991 |
| JP | 3-218399 A | 9/1991 |
| JP | 3-259084 A | 11/1991 |
| JP | 4-210700 A | 7/1992 |
| JP | 5-213998 A | 8/1993 |
| JP | 7-133289 A | 5/1995 |
| JP | 8-280384 A | 10/1996 |
| JP | 9-110900 A | 4/1997 |
| JP | 11-341990 A | 12/1999 |
| JP | 2007-16016 A | 1/2007 |
| JP | 2010-51927 A | 3/2010 |
| KR | 10-2009-0112709 A | 10/2009 |
| TW | 408129 B | 10/2000 |
| TW | 200801039 A | 1/2008 |
| TW | 200906848 A | 2/2009 |
| WO | WO 91/05803 A1 | 5/1991 |
| WO | WO 92/00325 A1 | 1/1992 |
| WO | WO 92/03149 A1 | 3/1992 |
| WO | WO 93/15755 A1 | 8/1993 |
| WO | WO 95/16460 A1 | 6/1995 |

(Continued)

OTHER PUBLICATIONS

Wouwer et al. (Aterioscler Thromb Vasc Biol, 2004).*
GE (Q-Sepharose).*
Uniprot (P07204 TRBM_HUMAN).*
Advantec (2008).*
International Search Report issued in PCT/JP2011/060348, dated Aug. 9, 2011.
Singapore Written Opinion, dated Aug. 1, 2013, for Patent Application No. 201207511-5.
Taiwanese Office Action and English translation therof, dated Aug. 9, 2013, for Patent Application No. 100114937.
Chinese Office Action dated Jan. 15, 2014 for Chinese Application No. 201180021497.X with English translation.
Extended European Search Report, dated Oct. 29, 2013, for European Application No. 11775094.3.
Pall Life Sciences, "Mustang Q XT Chromatography Capsules," Jan. 1, 2009, pp. 1-11, XP002713485.

(Continued)

*Primary Examiner* — Amber D Steele
*Assistant Examiner* — Schuyler Milton
(74) *Attorney, Agent, or Firm* — Birch, Stewart, Kolasch & Birch, LLP

(57) ABSTRACT

Highly-purified soluble thrombomodulin which has a content of host cell-originated proteins being in a ratio of less than 10 ng of the proteins per 10,000 U of the soluble thrombomodulin, wherein the soluble thrombomodulin is produced by a transformant cell obtained by transfecting a host cell with a DNA containing a nucleotide sequence encoding the soluble thrombomodulin.

28 Claims, No Drawings

(56) References Cited

FOREIGN PATENT DOCUMENTS

| WO | WO 2008/117735 A1 * | 10/2008 |
|----|---------------------|---------|
| WO | WO 2008/117735 A1   | 10/2008 |
| WO | WO 2009/030866 A2   | 3/2009  |

OTHER PUBLICATIONS

Australian Office Action dated Jul. 23, 2013 for Australian Application No. 2011246021.
Chinese Office Action dated May 16, 2013 for Chinese Application No. 201180021497.X with English translation.
New Zealand Office Action dated May 30, 2013 for New Zealand Application No. 602852.
Canadian Office Action, dated Mar. 27, 2014, for Canadian Application No. 2,796,452.
Japanese Office Action, dated Apr. 1, 2014, for Japanese Application No. 2012-512902.
Korean Office Action, dated Mar. 28, 2014, for Korean Application No. 10-2012-7030333.
Singapore Written Opinion, dated Apr. 14, 2014, for Singapore Application No. 2012075115.
Japanese Office Action mailed Feb. 24, 2015 for Japanese Application No. 2015-001499 with English language translation.
Japanese Office Action mailed Dec. 2, 2014 for Japanese Application No. 2012-512902 with English translation.
Bates et al., "New anticoagulants: beyond heparin, low-molecular-weight heparin and warfarin," British Journal of Pharmacology, vol. 144, No. 8, 2005, pp. 1017-1028.
Conway et al., "Biologically Active Thrombomodulin Is Synthesized by Adherent Synovial Fluid Cells and Is Elevated in Synovial Fluid of Patients With Rheumatoid Arthritis," Blood, vol. 81, No. 3, Feb. 1, 1993, pp. 726-733.
Full English translation of JP-11-341990-A dated Dec. 14, 1999.
Gomi et al., "Antithrombotic effect of recombinant human thrombomodulin on thrombin-induced thromboembolism in mice," Blood, vol. 75, No. 7, Apr. 1, 1990, pp. 1396-1399.
Hayakawa, "Development and Security of Quality and Safety of Biomedical Products," Life-Science Information Center, 2007, pp. 273-274 with partial English translation.
Huang et al, "Thrombomodulin-mediated Cell Adhesion, Involvement of Its Lectin-Like Domain," The Journal of Biological Chemistry, vol. 278, No. 47, Nov. 21, 2003, pp. 46750-46759.
International Preliminary Report on Patentability, and Translation of Written Opinion of the International Searching Authority, dated Dec. 20, 2012, for International Application No. PCT/JP2011/060348 (Forms PCT/IB/338, PCT/IB/373 and PCT/ISA/237).
Jackson et al., "Purification and characterization of two forms of soluble thrombomodulin from human urine," European Journal of Biochemistry, vol. 221, 1994, pp. 1079-1087.
Nadanaka et al., "Demonstration of the Immature Glycosaminoglycan Tetrasaccharide Sequence GlcAβ1-3Galβ1-3Galβ1-4Xyl on Recombinant Soluble Human α-Thrombomodulin," The Journal of Biological Chemistry, vol. 273, No. 50, Dec. 11, 1998, pp. 33728-33734.
Nawa et al., "Presence and Function of Chondroitin-4-Sulfate on Recombinant Human Soluble Thrombomodulin," Biochemical and Biophysical Research Communications, vol. 171, No. 2, Sep. 14, 1990, pp. 729-737.
Oetelaar et al., "Loss of Peptides and Proteins Upon Sterile Filtration Due to Adsorption to Membrane Filters," Drug Development and Industrial Pharmacy, vol. 15, No. 1, 1989, pp. 97-106.
Parkinson et al., "Stable Expression of a Secretable Deletion Mutant of Recombinant Human Thrombomodulin in Mammalian cells," The Journal of Biological Chemistry, vol. 265, No. 21, Jul. 25, 1990, pp. 12602-12610.
Saito et al., "Efficacy and safety of recombinant human soluble thrombomodulin (ART-123) in disseminated intravascular coagulation: results of a phase III, randomized, double-blind clinical trial," Journal of Thrombosis and Haemostasis, vol. 5, 2007, pp. 31-41.
Suzuki et al., "A Domain Composed of Epidermal Growth Factor-like Structures of Human Thrombomodulin Is Essential for Thrombin Binding and for Protein C Activation," The Journal of Biological Chemistry, vol. 264, No. 9, Mar. 25, 1989, pp. 4872-4876.
Suzuki, "New regulatory factors, protein C and its inhibitor, in blood coagulation and fibrinolysis," Igaku no Ayumi, vol. 125, No. 11, Jun. 11, 1983, pp. 901-910 with partial English translation.
Tabuchi et al., "Non-viral in vivo thrombomodulin gene transfer prevents early loss of thromboresistance of grafted veins," European Journal of Cardio-Thoracic Surgery, vol. 26, 2004 (available online: Aug. 25, 2004), pp. 995-1001.
Takahashi et al., "Soluble Thrombomodulin Purified from Human Urine Exhibits a Potent Anticoagulant Effect In Vitro and In Vivo," Thrombosis and Haemostasis, vol. 73, No. 5, 1995, pp. 805-811.
Wen et al., "Human Thrombomodulin: Complete cDNA Sequence and Chromosome Localization of the Gene," Biochemistry, vol. 26, Jul. 1, 1987, pp. 4350-4357.
White et al., "Large-scale expression, purification and characterization of small fragments of thrombomodulin: the roles of the sixth domain and of methionine 388," Protein Engineering, vol. 8, No. 11, 1995, pp. 1177-1187.
Yamamoto et al., "Urinary Thrombomodulin, Its Isolation and Characterization," The Journal of Biochemistry, vol. 113, No. 4, 1993, pp. 433-440.
Zushi et al., "The Last Three Consecutive Epidermal Growth Factor-like Structures of Human Thrombomodulin Comprise the Minimum Functional Domain for Protein C-activating Cofactor Activity . . . ," The Journal of Biological Chemistry, vol. 264, No. 18, Jun. 25, 1989, pp. 10351-10353.
Chinese Office Action dated Aug. 20, 2014 for Application No. 201180021497.X with English language translation.
Taiwanese Office Action dated Aug. 7, 2014 for Application No. 100114937 with English language translation.
Canadian Office Action for Application No. 2,796,452 dated Mar. 10, 2015.
Chinese Office Action for Application No. 201180021497.X dated Mar. 10, 2015 with English language translation.
Chen, Yinliang et al., "Continuous production of Thrombomodulin from a Pichia pastoris Fermentation", J. of. Chem. Tech. and Bio., vol. 67, No. 2, Oct. 1, 1996, pp. 143-148, XP000637775.
Schinkel, Helga et al., "Production of an active recombinant thrombomodulin derivative in transgenic tobacco plants and suspension cells", Transgenic Research, vol. 14, No. 3, Jun. 1, 2005, pp. 251-259, XP019269437.
Japanese Final Rejection issued in Japanese Application No. 2015-001499, dated Jul. 14, 2015, with English language translation.
European Office Action for corresponding European Application No. 11775094.3 dated Jun. 12, 2015.

* cited by examiner

HIGHLY-PURIFIED SOLUBLE THROMBOMODULIN AND METHOD FOR PRODUCING SAME

TECHNICAL FIELD

The present invention relates to highly-purified soluble thrombomodulin and a method for producing the same.

BACKGROUND ART

Thrombomodulin is known as a substance having an action of specifically binding to thrombin to inhibit the blood coagulation activity of thrombin, and at the same time, significantly promote the ability of thrombin to activate Protein C, and is also known to have strong blood coagulation-inhibiting action. It is also known that thrombomodulin extends the thrombin clotting time, and that it suppresses platelet aggregation by thrombin. Protein C is a vitamin K-dependent protein that plays an important role in the blood coagulation fibrinolytic system, and is activated by the action of thrombin to become activated Protein C. It is known that the activated Protein C inactivates activated blood coagulation factor V and activated blood coagulation factor VIII in vivo, and that it is involved in generation of plasminogen activator having thrombolytic action (Non-patent document 1). Therefore, thrombomodulin is considered to be useful as an anticoagulant agent or a thrombolytic agent that promotes the activation of Protein C by thrombin, and there have also been reported animal experiments demonstrating that thrombomodulin is effective for therapeutic and prophylactic treatments of diseases associated with acceleration of coagulation (Non-patent document 2).

Thrombomodulin was first discovered and obtained as a glycoprotein expressed on vascular endothelial cells of various animal species including human, and thereafter successfully cloned. More specifically, a human thrombomodulin precursor gene containing a signal peptide was cloned from a human lung cDNA library by genetic engineering techniques, and the entire gene sequence of thrombomodulin was analyzed, so that the amino acid sequence consisting of 575 residues containing a signal peptide (usually 18 amino acid residues are exemplified) was elucidated (Patent document 1). It is known that mature thrombomodulin, from which the signal peptide has been cleaved, is constituted by 5 regions, namely, an N-terminal region (amino acids 1 to 226, these positions are indicated on the assumption that the signal peptide consists of 18 amino acid residues, and the same shall apply to the other regions), a region having six EGF-like structures (amino acids 227 to 462), an O-linked glycosylation region (amino acids 463 to 498), a transmembrane region (amino acids 499 to 521), and an intracytoplasmic region (amino acids 522 to 557), from the N-terminal side of the mature peptide, and that a part having the same activity as that of the full length thrombomodulin (i.e., minimum unit for the activity) mainly consists of the 4th, 5th, and 6th EGF-like structure portions from the N-terminal side among the six EGF-like structures (Non-patent document 3).

Unless a surfactant is present, the full length thrombomodulin is hardly dissolved, and therefore addition of a surfactant is essential for producing a thrombomodulin preparation. In contrast, there is also soluble thrombomodulin that can be fully dissolved even in the absence of a surfactant. The soluble thrombomodulin may be prepared so as not to contain at least a part of the transmembrane region or the entire transmembrane region. For example, it has been confirmed that a soluble thrombomodulin consisting of only 3 regions of the N-terminal region, the region having six EGF-like structures, and the O-linked glycosylation region (i.e., soluble thrombomodulin having an amino acid sequence comprising amino acids at the positions 19 to 516 in SEQ ID NO: 1), can be obtained by applying recombination techniques, and that such recombinant soluble thrombomodulin has the same activity as that of the natural thrombomodulin (Patent document 1). In addition, there are also some other reports regarding soluble thrombomodulin (Patent documents 2 to 9). Further, human urine-derived soluble thrombomodulin and the like are also exemplified as natural thrombomodulin (Patent documents 10 and 11).

As recognized in many cases, as a result of spontaneous mutations or mutations occurring at the time of obtaining thrombomodulin, polymorphic mutations have been found even in human genes, and at present, such thrombomodulin genes that the amino acid at the position 473 of the human thrombomodulin precursor, that has the aforementioned amino acid sequence consisting of 575 amino acid residues, is Val or Ala have been identified. This difference corresponds to the difference of the nucleotide at the position 1418 to T or C in the nucleotide sequences encoding the amino acid (Non-patent document 4). However, these two thrombomodulins are completely identical in terms of their activities and physical properties. Thus, it can be considered that they are substantially identical.

It has been reported that thrombomodulin is effective for a therapeutic treatment of DIC (Non-patent documents 5 and 6). As for use of thrombomodulin, in addition to the aforementioned uses, thrombomodulin is expected to be used in therapeutic and prophylactic treatments of various diseases such as acute coronary syndrome (ACS), thrombosis, peripheral vessel obstruction, obstructive arteriosclerosis, vasculitis, functional disorder occurring after heart surgery, complication caused by organ transplantation, angina pectoris, transient ischemic attack, toxemia of pregnancy, diabetes, liver VOD (liver veno-occlusive disease, e.g., fulminant hepatitis, veno occlusive disease of liver occurring after bone marrow transplantation), and deep venous thrombosis (DVT), and further, adult respiratory distress syndrome (ARDS).

As a premise of application of thrombomodulin in pharmaceutical products, it is needless to explain that the soluble thrombomodulin is required to be manufactured in a large scale and at a cost as low as possible. However, there is also pointed out a possibility that heterogenous proteins originated in the production process, for example, proteins originated in host cells, bovine serum proteins originated in medium, and mouse IgG and the like originated in antibody column serve as immunogens to case problems concerning safety (Non-patent document 7).

As methods for producing soluble thrombomodulin in an industrial scale for application as a pharmaceutical product, there are known, for example, a method of using affinity column chromatography in a main purification step to which an antibody that reacts with thrombomodulin is bound, a method for producing highly purified soluble thrombomodulin substantially free from serum-originated substances and antibody-originated substances, which is characterized in that the soluble thrombomodulin is obtained as a flow-through fraction in a step of bringing the soluble thrombomodulin obtained by affinity column chromatography into contact with a cation exchanger under conditions of a specific conductivity of 25 to 34 ms/cm and pH 3 to 4 (Patent document 12), and a method for purifying thrombomodulin, wherein affinity column chromatography as the main purification step is followed by strong anion exchange chromatography (Patent document 13).

PRIOR ART REFERENCES

Patent Documents

Patent document 1: Japanese Patent Unexamined Publication (Kokai) No. 64-6219
Patent document 2: Japanese Patent Unexamined Publication No. 2-255699
Patent document 3: Japanese Patent Unexamined Publication No. 3-133380
Patent document 4: Japanese Patent Unexamined Publication No. 3-259084
Patent document 5: Japanese Patent Unexamined Publication No. 4-210700
Patent document 6: Japanese Patent Unexamined Publication No. 5-213998
Patent document 7: WO92/00325
Patent document 8: WO92/03149
Patent document 9: WO93/15755
Patent document 10: Japanese Patent Unexamined Publication No. 3-86900
Patent document 11: Japanese Patent Unexamined Publication No. 3-218399
Patent document 12: Japanese Patent Unexamined Publication No. 11-341990
Patent document 13: WO2008/117735

Non-Patent Documents

Non-patent document 1: Koji Suzuki, Igaku no Ayumi (Progress of Medicine), Vol. 125, 901 (1983)
Non-patent document 2: K. Gomi et al., Blood, 75, 1396-1399 (1990)
Non-patent document 3: M. Zushi et al., J. Biol. Chem., 264, 10351-10353 (1989)
Non-patent document 4: D. Z. Wen et al., Biochemistry, 26, 4350-4357 (1987)
Non-patent document 5: S. M. Bates et al., Br. J. Pharmacol., 144, 1017-1028 (2005)
Non-patent document 6: H. Saito et al., J. Thromb Haemost, 5 (1), 31 (2007)
Non-patent document 7: Akio Hayakawa, Development and Security of Quality and Safety of Biomedical Products, 273-274 (2007)

SUMMARY OF THE INVENTION

Object to be Achieved by the Invention

An object of the present invention is to provide highly-purified soluble thrombomodulin in which a concentration of proteins originated in host cells is a ratio of less than 10 ng of the proteins per 10,000 U of soluble thrombomodulin, and a method for producing the same.

Means for Achieving the Object

Patent document 13 describes purified soluble thrombomodulin. In particular, it discloses soluble thrombomodulin in which concentration of proteins originated in the host (henceforth also abbreviated as "HCP" in the specification) is indicated as "N.D." (this indication seems to mean "not detected", although it is not specifically indicated) in Example 14. Those skilled in the art who read this description would have normally considered that highly-purified soluble thrombomodulin containing reduced contamination of HCP was satisfactorily achieved, and would not have considered to further reduce HCP in soluble thrombomodulin, in other words, the artisans would not have been motivated to further reduce HCP in soluble thrombomodulin.

However, when the purified soluble thrombomodulin is used as a pharmaceutical product, the HCP, if contaminated in the product, might possibly cause unexpected condition such as anaphylactic shock, and might lead to a lethal risk, which the inventors of the present invention strongly recognized as a serious problem. From this reason, even under the circumstance that those skilled in the art would have normally considered that a contamination of HCP was sufficiently reduced as Patent document 13 mentioned above describes "N.D." in Example 14, the inventors of the present invention conducted measurement of a HCP concentration in the purified soluble thrombomodulin described in Example 14 of Patent document 13 mentioned above. As a result, although the concentration was almost near the detection limit, the contaminated HCP concentration was found to be a ratio of less than 70 to 80 ng per 10,000 U of the soluble thrombomodulin (henceforth "U" means a unit of the action for promoting activation of Protein C (henceforth also abbreviated as APC activity) as later described in Reference Example 1, unless otherwise specifically indicated), and thus the inventors of the present invention first recognized that improvement of the reduction of HCP might still be possibly achievable. The inventors of the present invention themselves consider that the HCP concentration can be accurately measured by employing an additional step of concentration in the HCP measurement step, which additional step is not disclosed in Patent document 13.

The inventors of the present invention who first discovered the aforementioned fact found a novel object to obtain purified thrombomodulin consisting of the soluble thrombomodulin having a further reduced HCP content to minimize the risk of anaphylactic shock, with the aim of safer use of soluble thrombomodulin as a pharmaceutical product.

The inventors of the present invention studied an application of an additional column chromatography step for industrial scale production of highly-purified soluble thrombomodulin in which contamination of HCP was further reduced. Specifically, they tried to reduce HCP by combining a plurality of column chromatography steps with affinity column chromatography considered to have the highest HCP-removing effect. However, such additional column chromatography steps not only increased the time and labor for the production, but also caused a problem of reduction of the yield of soluble thrombomodulin. Moreover, even if a plurality of column chromatography steps were combined with affinity column chromatography, highly-purified soluble thrombomodulin was not obtained in which the HCP concentration was further reduced compared with the conventional level. Furthermore, there also arose a problem that, in the column chromatography, only a small change of pH, ionic strength or the like resulted in a change of separation of HCP and soluble thrombomodulin, and thus an expected result was not successfully reproduced. Accordingly, it was difficult to obtain highly-purified soluble thrombomodulin.

Therefore, the inventors of the present invention conducted various researches to find a method for obtaining highly-purified soluble thrombomodulin containing further reduced contamination of HCP by efficiently eliminating HCP at an industrially acceptable level without reducing the yield of soluble thrombomodulin with a simpler operation compared with column chromatography. As a result, they found that the aforementioned object of obtaining highly-purified soluble thrombomodulin having an HCP concentration corresponding to a ratio of less than 10 ng of HCP per 10,000 U of soluble thrombomodulin was successfully achieved by using nylon and/or polyethersulfone, in particular, by using nylon, and thus accomplished the present invention.

The present invention is thus embodied as follows.

[1] Highly-purified soluble thrombomodulin which has a content of host cell-originated proteins being in a ratio of less than 10 ng of the proteins per 10,000 U of the soluble thrombomodulin, wherein the soluble thrombomodulin is produced by a transformant cell obtained by transfecting a host cell with a DNA containing a nucleotide sequence encoding the soluble thrombomodulin.

[1-2] The highly-purified soluble thrombomodulin according to [1] mentioned above, wherein purity of the highly-purified soluble thrombomodulin is 99% or higher based on the total proteins.

[1-3] The highly-purified soluble thrombomodulin according to [1] or [1-2] mentioned above, wherein the highly-purified soluble thrombomodulin is in the form of an aqueous solution.

[1-4] The highly-purified soluble thrombomodulin according to [1-3] mentioned above, wherein a concentration of soluble thrombomodulin in the aqueous solution of the highly-purified soluble thrombomodulin is 8 mg/mL or higher.

[2] The highly-purified soluble thrombomodulin according to any one of [1] to [1-4] mentioned above, wherein the soluble thrombomodulin is thrombomodulin produced by serum-free culture of the transformant cell.

When the referred item numbers are indicated with such a range as "[1] to [1-4]" mentioned above, and the range includes an item indicated with a number having a subnumber such as [1-2], it is meant that the item indicated with the number having a subnumber such as [1-2] is also cited. The same shall apply to the following definitions.

[2-2] The highly-purified soluble thrombomodulin according to any one of [1] to [2] mentioned above, wherein the concentration of host cell-originated proteins of less than 10 ng per 10,000 U of soluble thrombomodulin is confirmed by measuring content of the host cell-originated proteins by a method comprising at least the following steps:

(a) the step of preparing host cell-originated proteins from culture supernatant obtained by carrying out serum-free culture of a transformant cell obtained by transfecting the host cell with a DNA containing a nucleotide sequence encoding the soluble thrombomodulin, or the host cell, (b) the step of purifying an anti-host cell-originated protein antibody from antiserum obtained by sensitizing a rabbit with the host cell-originated proteins obtained in (a) mentioned above, the step of constructing a measurement system comprising:

(c1) the step of adsorbing the anti-host cell-originated protein antibody obtained in (b) mentioned above to a solid phase, (c2-1) the step of bringing a soluble thrombomodulin-containing test solution suspected to be contaminated with the host cell-originated proteins into contact with the solid phase to which the anti-host cell-originated protein antibody is adsorbed, and the step of bringing a solution containing the host cell-originated proteins of a known concentration into contact with the solid phase to which the anti-host cell-originated protein antibody is adsorbed, (c3) the step of adding a biotinylated anti-host cell-originated protein antibody to the solid phase, (c4) the step of adding a solution of avidinylated peroxidase to the solid phase, (c5) the step of adding an enzyme substrate solution to allow color development, and (c6) the step of terminating the color development and measuring absorbance, (d) the step of measuring concentration of the host cell-originated proteins in the soluble thrombomodulin-containing test solution suspected to be contaminated with the host cell-originated proteins in the aforementioned measurement system, and determining whether the concentration of the host cell-originated proteins in the soluble thrombomodulin-containing test solution is within a range that enables quantification of the proteins in the aforementioned measurement system, which range is confirmed beforehand by performing measurement using a solution of the host cell-originated proteins of a known concentration in the aforementioned measurement system, (e-1) the step of determining the concentration of the host cell-originated proteins in the soluble thrombomodulin-containing test solution suspected to be contaminated with the host cell-originated proteins as the concentration of the host cell-originated proteins in the solution, when the concentration is determined to be within the range that enables the quantification in (d) mentioned above, (e-2-1) the step of concentrating or diluting the soluble thrombomodulin-containing test solution suspected to be contaminated with the host cell-originated proteins, if desired, to make the concentration of the host cell-originated proteins to be a measurable concentration within the range that enables the quantification in the aforementioned measurement system, when the concentration of the host cell-originated proteins is determined to be not within the range that enables the quantification in (d) mentioned above, and recording the concentration ratio or dilution ratio, (e-2-2) the step of measuring the host cell-originated protein concentration in the soluble thrombomodulin-containing test solution concentrated or diluted in (e-2-1) mentioned above in a measurement system corresponding to the measurement system represented by the steps of (c1) to (c6) mentioned above in which (c2-1) is replaced with (c2-2) mentioned below, and obtaining the host cell-originated protein concentration with taking the concentration ratio or dilution ratio into consideration, (c2-2) the step of bringing the soluble thrombomodulin-containing test solution concentrated or diluted, if necessary, into contact with the solid phase to which the anti-host cell-originated protein antibody is adsorbed, and the step of bringing a solution containing the host cell-originated proteins of a known concentration into contact with the solid phase to which the anti-host cell-originated protein antibody is adsorbed, and (f) the step of calculating ratio of the host cell-originated protein concentration obtained in (e-1) or (e-2-2) based on APC activity of thrombomodulin per unit volume of the soluble thrombomodulin-containing test solution measured separately.

[2-3] The highly-purified soluble thrombomodulin according to [2-2] mentioned above, wherein the host cell mentioned in [2-2], (a) mentioned above is a cell of Chinese hamster ovary cell line DXB11.

[3] The highly-purified soluble thrombomodulin according to any one of [1] to [2-3] mentioned above, wherein the host cell is a Chinese hamster ovary cell.

[4] The highly-purified soluble thrombomodulin according to any one of [1] to [3] mentioned above, wherein the soluble thrombomodulin has the following properties (1) to (5):

(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[4-2] The highly-purified soluble thrombomodulin according to any one of [1] to [3] mentioned above, wherein the soluble thrombomodulin has the following properties (1) to (4):
(1) an action of selectively binding to thrombin,
(2) an action of promoting activation of Protein C by thrombin,
(3) an action of extending thrombin clotting time, and
(4) an action of suppressing platelet aggregation caused by thrombin.

[5] The highly-purified soluble thrombomodulin according to any one of [1] to [4-2] mentioned above, wherein molecular weight of the soluble thrombomodulin is 50,000 to 80,000.

[6] The highly-purified soluble thrombomodulin according to any one of [1] to [5] mentioned above, wherein the highly-purified soluble thrombomodulin is produced by a method comprising the following steps:
(a) the step of obtaining a transformant cell by transfecting a host cell with a DNA encoding a soluble thrombomodulin;
(b) the step of obtaining a solution containing the soluble thrombomodulin by culturing the transformant cell, and
(c) the step of bringing the solution containing the soluble thrombomodulin into contact with nylon and/or polyethersulfone to obtain highly-purified soluble thrombomodulin having a content of host cell-originated proteins being in a ratio of less than 10 ng of the proteins per 10,000 U of soluble thrombomodulin.

[7] The highly-purified soluble thrombomodulin according to any one of [1] to [6] mentioned above, wherein the soluble thrombomodulin is a peptide containing:
(i) the amino acid sequence of the positions 367 to 480 in the amino acid sequence of SEQ ID NO: 9 or 11, and the amino acid sequence of (ii-1) or (ii-2) mentioned below, and the peptide is soluble thrombomodulin having the following properties (1) to (5):
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues,
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[7-2] The highly-purified soluble thrombomodulin according to any one of [1] to [6] mentioned above, wherein the soluble thrombomodulin is a peptide containing:
(i) the amino acid sequence of the positions 367 to 480 in the amino acid sequence of SEQ ID NO: 9 or 11, and the amino acid sequence of (ii-1) or (ii-2) mentioned below, and the peptide is soluble thrombomodulin having the following properties (1) to (4):
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues,
(1) an action of selectively binding to thrombin,
(2) an action of promoting activation of Protein C by thrombin,
(3) an action of extending thrombin clotting time, and
(4) an action of suppressing platelet aggregation caused by thrombin.

[7-3] The highly-purified soluble thrombomodulin according to any one of [1] to [6] mentioned above, wherein the soluble thrombomodulin is a peptide containing the amino acid sequence of (i-1) or (i-2) mentioned below, and containing the amino acid sequence of (ii-1) or (ii-2) mentioned below, and the peptide is soluble thrombomodulin having the properties (1) to (5) mentioned below:
(i-1) the amino acid sequence of the positions 367 to 480 in the amino acid sequence of SEQ ID NO: 9 or 11, or
(i-2) the amino acid sequence of (i-1) mentioned above, further including substitution, deletion or addition of one or more amino acid residues,
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues,
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[8] The highly-purified soluble thrombomodulin according to any one of [1] to [6] mentioned above, wherein the soluble thrombomodulin is a peptide containing:
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues,
and the peptide is soluble thrombomodulin having the properties (1) to (5) mentioned below:
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[9] The highly-purified soluble thrombomodulin according to any one of [1] to [6] mentioned above, wherein the DNA containing a nucleotide sequence encoding soluble thrombomodulin is a DNA encoding the amino acid sequence of SEQ ID NO: 9 or 11.

[10] A pharmaceutical composition containing the highly-purified soluble thrombomodulin according to any one of [1] to [9] mentioned above and a pharmaceutically acceptable carrier.

[11] A method for preparing highly-purified soluble thrombomodulin having a content of host cell-originated proteins being in a ratio of less than 10 ng of the proteins per 10,000 U of soluble thrombomodulin, which comprises the step of bringing a solution containing soluble thrombomodulin produced by a transformant cell obtained by transfecting a host cell with a DNA containing a nucleotide sequence encoding soluble thrombomodulin into contact with nylon and/or polyethersulfone.

[12] The preparation method according to [11] mentioned above, wherein the soluble thrombomodulin is prepared by serum-free culture of the transformant cell.

[13] The method for preparing highly-purified soluble thrombomodulin according to [11] or [12] mentioned above, wherein the soluble thrombomodulin has the following properties (1) to (5);
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[14] The preparation method according to any one of [11] to [13] mentioned above, wherein the host cell is a Chinese hamster ovary cell.

[15] The preparation method according to any one of [11] to [14] mentioned above, wherein molecular weight of the soluble thrombomodulin is 50,000 to 80,000.

[16] The preparation method according to any one of [11] to [15] mentioned above, wherein the soluble thrombomodulin is a peptide containing:
(i) the amino acid sequence of the positions 367 to 480 in the amino acid sequence of SEQ ID NO: 9 or 11, and the amino acid sequence of (ii-1) or (ii-2) mentioned below, and the peptide is soluble thrombomodulin having the following properties (1) to (5):
(ii-1) the amino acid sequence of the positions 19 to 244 in the amino acid sequence of SEQ ID NO: 9 or 11, or
(ii-2) the amino acid sequence of (ii-1) mentioned above, further including substitution, deletion or addition of one or more amino acid residues,
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[17] The preparation method according to any one of [11] to [15] mentioned above, wherein the soluble thrombomodulin is a peptide containing:
(i-1) the amino acid sequence of the positions 19 to 516 in the amino acid sequence of SEQ ID NO: 9 or 11, or
(i-2) the amino acid sequence of (i-1) mentioned above, further including substitution, deletion or addition of one or more amino acid residues, and
the peptide is soluble thrombomodulin having the properties (1) to (5) mentioned below:
(1) an action of selectively binding to thrombin,
(2) an action of promoting activation of Protein C by thrombin,
(3) an action of extending thrombin clotting time,
(4) an action of suppressing platelet aggregation caused by thrombin, and
(5) anti-inflammatory action.

[18] The preparation method according to any one of [11] to [15] mentioned above, wherein the DNA containing a nucleotide sequence encoding soluble thrombomodulin is a DNA encoding the amino acid sequence of SEQ ID NO: 9 or 11.

[19] The preparation method according to any one of [11] to [18] mentioned above, wherein the nylon and/or polyethersulfone is in the form of a filtration membrane.

[20] The preparation method according to [19] mentioned above, wherein the filtration membrane has a membrane area of 0.01 to 0.5 $m^2$ for 1 mg of the host cell-originated proteins.

[21] The preparation method according to any one of [11] to [20] mentioned above, wherein the nylon and/or polyethersulfone is nylon.

[22] The preparation method according to any one of [11] to [20] mentioned above, which has the characteristics described in any one of [1-2] to [1-4], [2-2], [2-3], [7-2] and [7-3].

[23] The preparation method according to any one of [11] to [22] mentioned above, which is a method for preparing highly-purified soluble thrombomodulin having a content of host cell-originated proteins being in a ratio of less than 10 ng of the proteins per 10,000 U of soluble thrombomodulin, comprising:
(a) the step of obtaining a transformant cell by transfecting a host cell with a DNA encoding the amino acid sequence of SEQ ID NO: 9 or 11,
(b) the step of obtaining a solution containing soluble thrombomodulin by culturing the transformant cell,
(c) the step of purifying the solution containing soluble thrombomodulin to obtain a thrombomodulin purity of 99% or higher based on the total proteins, and
(d) the step of bringing the solution containing soluble thrombomodulin into contact with nylon to isolate highly-purified soluble thrombomodulin having a content of host cell-originated proteins being in a ratio of less than 10 ng of the proteins per 10,000 U of soluble thrombomodulin, and
wherein the host cell is a Chinese hamster ovary cell.

[24] Highly-purified soluble thrombomodulin producible by the method according to [23] mentioned above.

[25] A method for removing host cell-originated proteins in soluble thrombomodulin, which comprises the step of bringing a solution containing soluble thrombomodulin produced by a transformant cell obtained by transfecting a host cell with a DNA containing a nucleotide sequence encoding soluble thrombomodulin into contact with nylon and/or polyethersulfone.

[26] A method for removing host cell-originated proteins in soluble thrombomodulin, which comprises:
(a) the step of obtaining a transformant cell by transfecting a host cell with a DNA encoding the amino acid sequence of SEQ ID NO: 9 or 11,
(b) the step of obtaining a solution containing soluble thrombomodulin by culturing the transformant cell,
(c) the step of purifying the solution containing soluble thrombomodulin to a thrombomodulin purity of 99% or higher based on the total proteins, and
(d) the step of bringing the solution containing soluble thrombomodulin into contact with nylon, and
wherein the host cell is a Chinese hamster ovary cell.

[27] The method for removing host cell-originated proteins in soluble thrombomodulin according to [25] mentioned above, which has the characteristics mentioned in any one of [1] to [9] mentioned above.

Effect of the Invention

By using the preparation method of the present invention, highly-purified soluble thrombomodulin of reduced contamination of host cell-originated proteins having a content of host cell-originated proteins being in a ratio of less than 10 ng of the proteins per 10,000 U of soluble thrombomodulin can be obtained. The risk of anaphylactic shock at the time of using soluble thrombomodulin as a pharmaceutical product can be thereby further reduced.

MODES FOR CARRYING OUT THE INVENTION

Hereafter, several preferred embodiments of the present invention (preferred modes for carrying out the invention, henceforth also referred to as "embodiments" in this specification) will be specifically explained. However, the scope of the present invention is not limited to the specific embodiments explained below.

The highly-purified soluble thrombomodulin of this embodiment can be used as a material for a medicament. The highly-purified soluble thrombomodulin of this embodiment can also be combined with another pharmaceutically acceptable carrier and used as a pharmaceutical product.

Further, the highly-purified soluble thrombomodulin of this embodiment can be used as a highly-purified soluble thrombomodulin-containing pharmaceutical composition not substantially containing any substances other than the soluble thrombomodulin. The highly-purified soluble thrombomodulin of this embodiment can also be combined with another pharmaceutically acceptable carrier and used as a pharmaceutical composition.

Hereafter, the term of highly-purified soluble thrombomodulin may include highly-purified soluble thrombomodulin as a material for a medicament. The term of highly-purified soluble thrombomodulin may also include a highly-purified soluble thrombomodulin-containing pharmaceutical composition not substantially containing any substances other than the soluble thrombomodulin.

The thrombomodulin of this embodiment preferably is known to have an action of (1) selectively binding to thrombin (2) to promote activation of Protein C by thrombin. In addition, it is preferred that the thrombomodulin is confirmed to generally have (3) an action of extending thrombin clotting time, (4) an action of suppressing platelet aggregation caused by thrombin, and/or (5) anti-inflammatory action. Such actions possessed by thrombomodulin may be referred to as thrombomodulin activities.

As the thrombomodulin activities, thrombomodulin preferably has the actions of (1) and (2) mentioned above, and more preferably has the actions of (1) to (4) mentioned above. As the thrombomodulin activities, thrombomodulin more preferably has all of the actions of (1) to (5) mentioned above.

The action of thrombomodulin to bind with thrombin can be confirmed by the test methods described in various known publications such as Thrombosis and Haemostasis, 70(3): 418-422 (1993). As for the action of promoting activation of Protein C by thrombin, degree of the activity of promoting the activation of Protein C by thrombin or presence or absence of the action can be easily confirmed by the test methods clearly described in various known publications including, for example, Japanese Patent Unexamined Publication No. 64-6219. Further, the action of extending thrombin clotting time, and/or the action of suppressing platelet aggregation caused by thrombin can be similarly and easily confirmed. Furthermore, the anti-inflammatory action can also be confirmed by the test methods described in various known publications including, for example, Blood, 112:3361-3670 (2008) and The Journal of Clinical Investigation, 115, 5:1267-1274 (2005).

An example of the soluble thrombomodulin includes a soluble thrombomodulin that is soluble in water in the absence of a surfactant. For example, the solubility of soluble thrombomodulin is preferably 1 mg/ml or higher, or 10 mg/ml or higher in water, for example, in distilled water used for injection (in general, around a neutral range in the absence of a surfactant such as Triton X-100 or Polidocanol). The solubility is more preferably 15 mg/ml or higher, or 17 mg/ml or higher; still more preferably 20 mg/ml or higher, 25 mg/ml or higher, or 30 mg/ml or higher; and mostly preferably 60 mg/ml or higher. In some cases, the solubility may be 80 mg/ml or higher, or 100 mg/ml or higher. For determining whether or not soluble thrombomodulin can be dissolved, the solution can be observed with the naked eye, for example, directly below white light source, at a position of brightness of approximately 1,000 lux after the soluble thrombomodulin is dissolved, and it can be understood that transparency of the resulting solution and no contamination of apparently observable insoluble substances may be clear criteria of dissolution. In addition, it is also possible to filtrate the solution to confirm the presence or absence of a residue.

The molecular weight of the soluble thrombomodulin is not limited so far that it has the thrombomodulin activities and is soluble as described above. The molecular weight is preferably 100,000 or smaller, more preferably 90,000 or smaller, still more preferably 80,000 or smaller, most preferably 70,000 or smaller, and the molecular weight is preferably 50,000 or larger, most preferably 60,000 or larger. The molecular weight of the soluble thrombomodulin can be easily measured by ordinary methods for measuring molecular weight of protein. Measurement by mass spectrometry is preferred, and MALDI-TOF-MS method is more preferred.

For obtaining soluble thrombomodulin having a molecular weight within a desired range, a soluble thrombomodulin, which is obtained by culturing a transformant cell prepared by transfecting a host cell with a DNA encoding soluble thrombomodulin using a vector, can be subjected to fractionation using column chromatography or the like as described later.

As the soluble thrombomodulin, those of the human-type thrombomodulin are preferred which include the amino acid sequence of the positions 19 to 132 in SEQ ID NO: 1 together with the amino acid sequence of the positions 19 to 244 in SEQ ID NO: 9 or 11 or said amino acid sequence further including substitution, deletion or addition of one or more amino acid residues. The amino acid sequence of the positions 19 to 132 in SEQ ID NO: 1 participates in the action of promoting activation of Protein C by thrombin among the thrombomodulin activities. The amino acid sequence of the positions 19 to 244 in SEQ ID NO: 9 or 11 participates in the anti-inflammatory action among the thrombomodulin activities. So far that the soluble thrombomodulin has the thrombomodulin activities as the whole soluble thrombomodulin, the amino acid sequence of the positions 19 to 132 in SEQ ID NO: 1 may be naturally or artificially mutated, namely, the amino acid sequence of the positions 19 to 132 in SEQ ID NO: 1 may include substitution, deletion or addition of one or more amino acid residues. Acceptable degree of the mutation is not particularly limited so far that the soluble thrombomodulin has the thrombomodulin activities, for example, including homology of 50% or higher based on an amino acid sequence, preferably homology of 70% or higher, more preferably homology of 80% or higher, further preferably homology of 90% or higher, further more preferably homology of 95% or higher, and most preferably homology of 98% or higher. Such mutated amino acid sequence including substitution, deletion or addition of one or more amino acid residues is referred to as homologous mutation sequence. As described later, these mutated amino acid sequences can be easily produced by using ordinary gene manipulation techniques. The soluble thrombomodulin is not particularly limited so far that it has the aforementioned sequence and the action of selectively binding to thrombin to promote activation of Protein C by thrombin at least as the whole soluble thrombomodulin. The soluble thrombomodulin preferably also has the anti-inflammatory action.

In the amino acid sequence of SEQ ID NO: 3, Val as the amino acid at the position 125 in the amino acid sequence of SEQ ID NO: 1 is replaced by Ala. It is also preferred that the thrombomodulin of this embodiment contains the amino acid sequence of the positions 19 to 132 in SEQ ID NO: 3.

As described above, the soluble thrombomodulin is not particularly limited, so far that it has at least the sequence of the positions 19 to 132 in SEQ ID NO: 1 or 3, or a homologous mutation sequence thereof, and the amino acid sequence of the positions 19 to 244 in SEQ ID NO: 9 or 11, or a homologous mutation sequence thereof, and has at least the action of selectively binding to thrombin to promote activation of Protein C by thrombin as the whole soluble thrombomodulin. Preferred examples include a peptide comprising the sequence of the positions 19 to 132 or the positions 17 to 132 in SEQ ID NO: 1 or 3, or a homologous mutation sequence thereof, and the amino acid sequence of the positions 19 to 244 in SEQ ID NO: 9 or 11 or a homologous mutation sequence thereof, and having the thrombomodulin activities at least as the whole soluble thrombomodulin, and a peptide comprising the sequence of the positions 19 to 132 in SEQ ID NO: 1 or 3 and the amino acid sequence of the positions 19 to 244 in SEQ ID NO: 9 or 11 or a homologous mutation sequence thereof is more preferred. There is also another embodiment in which a peptide comprising the sequence of the positions 19 to 132 or the positions 17 to 132 in SEQ ID NO: 1 or 3 or a homologous mutation sequence thereof, and the amino acid sequence of the positions 19 to 244 in SEQ ID NO: 9 or 11 or a homologous mutation sequence, and having the thrombomodulin activities at least as the whole soluble thrombomodulin, which is sometimes more preferred.

It is preferred that the soluble thrombomodulin also has the anti-inflammatory action as the whole soluble thrombomodulin.

As another embodiment, the thrombomodulin preferably contains the amino acid sequence of the positions 19 to 480 in SEQ ID NO: 5, and such thrombomodulin is not particularly limited so far that it contains the amino acid sequence of the positions 19 to 480 in SEQ ID NO: 5. The amino acid sequence of the positions 19 to 480 in SEQ ID NO: 5 may be a homologous mutation sequence so far that it has the thrombomodulin activities.

The amino acid sequence of SEQ ID NO: 7 corresponds to the amino acid sequence of SEQ ID NO: 5 in which Val as the amino acid at the position 473 is replaced with Ala. The soluble thrombomodulin of this embodiment also preferably contains the amino acid sequence of the positions 19 to 480 in SEQ ID NO: 7.

As described above, the soluble thrombomodulin is not particularly limited so far that it has at least the amino acid sequence of the positions 19 to 480 in SEQ ID NO: 5 or 7, or a homologous mutation sequence thereof, and contains a peptide sequence having at least the thrombomodulin activities. Preferred examples include a peptide comprising the sequence of the positions 19 to 480 or the positions 17 to 480 in SEQ ID NO: 5 or 7, or a homologous mutation sequence thereof, and having at least the thrombomodulin activities, and a peptide comprising the sequence of the positions 19 to 480 in SEQ ID NO: 5 or 7 is more preferred. There is also another embodiment in which a peptide comprising a homologous mutation sequence of the sequence of the positions 19 to 480 or the positions 17 to 480 in SEQ ID NO: 5 or 7 and having at least the thrombomodulin activity, which is sometime mores preferred.

It is preferred that the soluble thrombomodulin also has the anti-inflammatory action.

As another particularly preferred embodiment, the soluble thrombomodulin preferably contains the amino acid sequence of the positions 19 to 515 in SEQ ID NO: 9, and such soluble thrombomodulin is not particularly limited so far that it contains the amino acid sequence of the positions 19 to 515 in SEQ ID NO: 9. The amino acid sequence of the positions 19 to 515 o in SEQ ID NO: 9 may be a homologous mutation sequence thereof so far that it has the thrombomodulin activities.

The amino acid sequence of SEQ ID NO: 11 corresponds to the amino acid sequence of SEQ ID NO: 9 in which Val as the amino acid at the position 473 is replaced with Ala. The soluble thrombomodulin of this embodiment also preferably contains the amino acid sequence of the positions 19 to 515 in SEQ ID NO: 11.

As described above, the soluble thrombomodulin is not particularly limited so far that it contains a peptide having at least the amino acid sequence of the positions 19 to 515 in SEQ ID NO: 9 or 11, or a homologous mutation sequence thereof, and having at least the thrombomodulin activities. More preferred examples include a peptide comprising the amino acid sequence of the positions 19 to 516, 19 to 515, 19 to 514, 17 to 516, 17 to 515, or 17 to 514 in SEQ ID NO: 9 or 11, or a peptide comprising a homologous mutation sequence thereof and having at least the thrombomodulin activities, and a peptide comprising the amino acid sequence of the positions 19 to 516, 19 to 515, 19 to 514, 17 to 516, 17 to 515, or 17 to 514 in SEQ ID NO: 9 is particularly preferred. In addition, a mixture thereof is also a preferred example. There is another preferred embodiment in which a peptide comprising the amino acid sequence of the positions 19 to 516, 19 to 515, 19 to 514, 17 to 516, 17 to 515, or 17 to 514 in SEQ ID NO: 11, which is particularly preferred. A mixture thereof is also a preferred example. Further, a peptide comprising a homologous mutation sequence thereof and having at least the thrombomodulin activities is also another preferred example.

It is preferred that the soluble thrombomodulin also has the anti-inflammatory action.

A peptide having a homologous mutation sequence is as described above. Such a peptide having a homologous mutation sequence also includes a peptide that may include substitution, deletion, or addition of one or more, namely, one or multiple, more preferably several (for example, 1 to 20, preferably 1 to 10, more preferably 1 to 5, most preferably 1 to 3) amino acid residues in the amino acid sequence of the target peptide. Acceptable degree of mutation is not particularly limited so far that the peptide has the thrombomodulin activities. Examples include, for example, homology of 50% or higher, preferably homology of 70% or higher, more preferably homology of 80% or higher, further preferably homology of 90% or higher, further more preferably homology of 95% or higher, and most preferably homology of 98% or higher based on an amino acid sequence.

As the soluble thrombomodulin, preferred examples further include a peptide comprising the sequence of SEQ ID NO: 14 (462 amino acid residues), a peptide comprising the sequence of SEQ ID NO: 8 (272 amino acid residues), and a peptide comprising the sequence of SEQ ID NO: 6 (236 amino acid residues) described in Japanese Patent Unexamined Publication No. 64-6219.

The soluble thrombomodulin is not particularly limited so far that it is a peptide having at least the sequence of the positions 19 to 132 in SEQ ID NO: 1 or 3, or a homologous mutation sequence thereof, and the amino acid sequence of the positions 19 to 244 in SEQ ID NO: 9 or 11, or a homologous mutation sequence thereof, and has the thrombomodulin activities at least as the whole soluble thrombomodulin. A peptide comprising at least the amino acid sequence of the positions 19 to 480 in SEQ ID NO: 5 or 7 is preferred, and a peptide comprising at least the amino acid sequence of the positions 19 to 515 in SEQ ID NO: 9 or 11 is more preferred. More preferred examples of the peptide comprising at least the amino acid sequence of the positions 19 to 515 in SEQ ID NO: 9 or 11 include a peptide comprising the amino acid sequence of the positions 19 to 516, 19 to 515, 19 to 514, 17 to 516, 17 to 515, or 17 to 514 in SEQ ID NO: 9 or 11. More preferred examples also include a mixture of peptides comprising the amino acid sequence of the positions 19 to 516, 19 to 515, 19 to 514, 17 to 516, 17 to 515, or 17 to 514 for each of SEQ ID NOS: 9 and 11.

In the case of the aforementioned mixture, the mixing ratio of a peptide that starts from the position 17 and a peptide that starts from the position 19 for each of SEQ ID NOS: 9 and 11 is, for example, 30:70 to 50:50, preferably 35:65 to 45:55.

Further, the mixing ratio of a peptide that terminates at the position 514, a peptide that terminates at the position 515, and a peptide that terminates at the position 516 for each of SEQ ID NOS: 9 and 11 is, for example, 0:0:100 to 0:90:10, or 0:70:30 to 10:90:0, or 10:0:90 to 20:10:70, if desired.

The mixing ratio of the peptides can be determined by an ordinary method.

The sequence of the positions 19 to 132 in SEQ ID NO: 1 corresponds to the sequence of the positions 367 to 480 in SEQ ID NO: 9, and the sequence of the positions 19 to 480 in SEQ ID NO: 5 corresponds to the sequence of the positions 19 to 480 in SEQ ID NO: 9.

Further, the sequence of the positions 19 to 132 in SEQ ID NO: 3 corresponds to the sequence of the positions 367 to 480 in SEQ ID NO: 11, and the sequence of the positions 19 to 480 in SEQ ID NO: 7 corresponds to the sequence of the positions 19 to 480 in SEQ ID NO: 11.

Furthermore, all the sequences of the positions 1 to 18 in SEQ ID NOS: 1, 3, 5, 7, 9 and 11 are identical sequences.

These soluble thrombomodulin can be obtained, for example, from a transformant cell prepared by transfecting a host cell with a DNA encoding any of those peptides (specifically, a nucleotide sequence having the nucleotide sequence of the positions 1 to 732 in SEQ ID NO: 10 and the nucleotide sequence of the positions 55 to 396 in SEQ ID NO: 2, a nucleotide sequence having the nucleotide sequence of the positions 1 to 732 in SEQ ID NO: 10 and the nucleotide sequence of the positions 55 to 396 in SEQ ID NO: 4, a nucleotide sequence of SEQ ID NO: 6, 8, 10 or 12) using a vector, as described later.

It is sufficient that these peptides have any of the aforementioned amino acid sequences. A sugar chain may be or may not be added, and the peptides are not particularly limited in this respect. In addition, in gene manipulation, type of such a sugar chain, position to which a sugar chain is added, and degree of addition may vary depending on the type of the host cell used, and they are not particularly limited. The binding position of such a sugar chain and the type thereof are described in Japanese Patent Unexamined Publication No. 11-341990, and in the case of the thrombomodulin of this embodiment, similar sugar chains may be added to similar positions. Two types of N-linked sugar chains, those of fucosyl biantennary type and fucosyl triantennary type, may bind to the soluble thrombomodulin of this embodiment, and ratio thereof is, for example, 100:0 to 60:40, preferably 95:5 to 60:40, more preferably 90:10 to 70:30. The ratio of these sugar chains can be measured on a two-dimensional sugar chain map described in Biochemical Experimental Methods, Vol. 23, Methods of Researches on Glycoprotein Sugar Chains, Japan Scientific Societies Press (1990), and the like. Furthermore, when a sugar composition of the soluble thrombomodulin of this embodiment is examined, neutral saccharides, aminosaccharides, and sialic acid is detected, of which content may be, each independently for example, 1 to 30%, preferably 2 to 20%, more preferably 5 to 10% in terms of weight ratio based on a protein content. The sugar contents can be measured by the methods described in Lecture of New Biochemical Experiments, Vol. 3, Sugar I, Glycoprotein (Book 1), Tokyo Kagaku Dojin (1990) (neutral saccharides: phenol-sulfuric acid method, aminosaccharides: Elson-Morgan method, sialic acid: periodic acid-resorcinol method).

As a signal sequence that can be used for expression where the soluble thrombomodulin is obtained by gene manipulation, a nucleotide sequence encoding the amino acid sequence of the positions 1 to 18 in SEQ ID NO: 9, and a nucleotide sequence encoded by a nucleotide sequence encoding the amino acid sequence of the positions 1 to 16 in SEQ ID NO: 9 can be used, and other known signal sequences such as the signal sequence of human tissue plasminogen activator can also be used (International Publication WO88/9811).

When a DNA sequence encoding soluble thrombomodulin is introduced into a host cell, there is preferably used a method of incorporating the DNA sequence encoding soluble thrombomodulin into a vector, more preferably an expression vector that can be expressed in animal cells, and then introducing the vector into the host cell. The term "expression vector" means a DNA molecule constituted by a promoter sequence, a sequence for adding a ribosome binding site to mRNA, a DNA sequence encoding a protein to be expressed, a splicing signal, a terminator sequence for transcription termination, a replication origin sequence, and the like. Examples of a preferred animal cell expression vector include pSV2-X reported by R. C. Mulligan et al. (Proc. Natl. Acad. Sci. U.S.A. 78, 2072 (1981)) and pBP69T (69-6) reported by P. M. Howley et al. (Methods in Emzymology, 101, 387, Academic Press (1983)). Further, there is also another preferred embodiment in which DNA is introduced into an expression vector expressible in a microorganism.

Examples of host cell that can be used in production of such peptides as mentioned above include animal cells.

Examples of the animal cells include Chinese hamster ovary (CHO) cells, COS-1 cells, COS-7 cells, VERO (ATCC CCL-81) cells, BHK cells, canine kidney-derived MDCK cells, hamster AV-12-664 cells, NS0 cells, and the like. In addition, examples of host cell derived from human include HeLa cells, WI38 cells, human 293 cells, and PER.C6 cells. Of these cells, CHO cells are very common and preferred, and among the CHO cells, dihydrofolate reductase (DHFR)-deficient CHO cells are more preferred.

In a gene manipulation process or a peptide production process, microorganisms such as *Escherichia coli* are also often used. A host-vector system suitable for each process is preferably used, and an appropriate vector system can also be selected for the aforementioned host cells. A thrombomodulin gene used in a genetic recombination technique has been cloned. Examples of production of thrombomodulin by such a gene recombination technique have been disclosed, and further, methods for purifying thrombomodulin to obtain a purified product thereof are also known (Japanese Patent Unexamined Publication Nos. 64-6219, 2-255699, 5-213998, 5-310787, 7-155176; and J. Biol. Chem., 264: 10351-10353 (1989)). Therefore, the soluble thrombomodulin used for this embodiment can be produced by using the methods described in the aforementioned reports, or by similar methods. For example, Japanese Patent Unexamined Publication No. 64-6219 discloses the *Escherichia coli* K-12 strain DH5 (ATCC Accession No. 67283) containing a plasmid pSV2TMJ2 that contains a DNA encoding the full-length thrombomodulin. This strain re-deposited at the former National Institute of Bioscience and Human-Technology (currently Independent Administrative Institution, National Institute of Advanced Industrial Science and Technology, International Patent Organism Depositary) (*Escherichia coli* DH5/pSV2TMJ2) (FERM BP-5570) can also be used. The thrombomodulin of this embodiment can be prepared by a known gene manipulation technique using a DNA encoding the full-length thrombomodulin as a starting material.

The soluble thrombomodulin may be prepared by a conventionally known method or a similar method. For example, the aforementioned method of Yamamoto et al. (Japanese Patent Unexamined Publication No. 64-6219) or the method described in Japanese Patent Unexamined Publication No. 5-213998 can be referred to. Specifically, for example, a DNA encoding the amino acid sequence of SEQ ID NO: 9 is prepared from a human-derived soluble thrombomodulin gene by a gene manipulation technique, and may be further modified as required. For such modification, in order to obtain a DNA encoding the amino acid sequence of SEQ ID NO: 11 (which specifically consists of the nucleotide sequence of SEQ ID NO: 12), codons encoding the amino acid at the position 473 in the amino acid sequence of SEQ ID NO: 9 (in particular, the nucleotide at the position 1418) are mutated by site-directed mutagenesis according to the method described in Methods in Enzymology, 100: 468 (1983), Academic Press. For example, by using a synthetic DNA for mutation having the nucleotide sequence of SEQ ID NO: 13, the nucleotide T at the position 1418 in SEQ ID NO: 10 may be converted to the nucleotide C to obtain a mutated DNA.

The DNA prepared as described above is incorporated into, for example, Chinese hamster ovary (CHO) cells to obtain transformant cells. Such cells are subjected to appropriate selection, and soluble thrombomodulin purified by a known method can be produced from a culture solution obtained by culturing a selected cell. As described above, the DNA (SEQ ID NO: 10) encoding the amino acid sequence of SEQ ID NO: 9 is preferably transfected into the aforementioned host cell.

For the culture of the aforementioned transformant cell, a medium used for ordinary cell culture may be used, and it is preferable to culture the transformant cell in various kinds of media in advance to choose an optimal medium. For example, a known medium such as MEM medium, DMEM medium, and 199 medium may be used as a base medium, and a further improved medium or a medium added with supplements for various media may be used. Examples of the culture method include serum culture, in which culture is performed in a medium containing blood serum, and serum-free culture, in which culture is performed in a medium not containing blood serum. Although the culture method is not particularly limited, the serum-free culture is preferred.

When serum is added to a medium in the case of the serum culture, bovine serum is preferred. Examples of bovine serum include fetal bovine serum, neonate bovine serum, calf bovine serum, adult bovine serum, and the like, and any of these examples may be used so far that the serum is suitable for the cell culture. As the serum-free medium used in the serum-free culture, commercially available media can be used. Serum-free media suitable for various cells are marketed, and for example, for the CHO cell, CD-CHO, CHO-S-SFMII and CHO-III-PFM are sold by Invitrogen, and IS CHO, IS CHO-CD medium, and the like are sold by Irvine Scientific. These media may be used without any treatment, or they may be improved or added with supplements and used. Examples of the serum-free medium further include the DMEM medium containing 5 mg/L each of insulin, transferrin, and selenious acid. As described above, the medium is not particularly limited so far that the medium can be used to produce the thrombomodulin of this embodiment. The culture method is not particularly limited, and any of batch culture, repetitive batch culture, fed-batch culture, perfusion culture, and the like may be used.

When the soluble thrombomodulin is prepared by the aforementioned cell culture method, diversity may be observed in the N-terminus amino acid due to posttranslational modification of the protein. For example, the amino acid of the position 17, 18, 19 or 22 in SEQ ID NO: 9 may serve as the N-terminus amino acid. Further, for example, the N-terminus amino acid may be modified so that the glutamic acid at the position 22 is changed to pyroglutamic acid. It is preferred that the amino acid of the position 17 or 19 serves as the N-terminus amino acid, and it is more preferred that the amino acid of the position 19 serves as the N-terminus amino acid. Further, there is also another embodiment in which the amino acid of the position 17 serves as the N-terminus amino acid, which is a preferred embodiment. As for the modification, diversity and the like mentioned above, similar examples can be mentioned for the sequence of SEQ ID NO: 11.

Further, when the soluble thrombomodulin is prepared by using a DNA having the nucleotide sequence of SEQ ID NO: 10, diversity of the C-terminus amino acid may be observed, and a peptide shorter by one amino acid residue may be produced. Specifically, the C-terminus amino acid may be modified so that the amino acid of the position 515 serves as the C-terminus amino acid, and further the position 515 is amidated. Further, a peptide shorter by two amino acid residues may be produced. Specifically, the amino acid of the position 514 may serve as the C-terminus amino acid. Therefore, any of peptides having significant diversity of the N-terminus amino acid and C-terminus amino acid, or a mixture of them may be produced. It is preferred that the amino acid of the position 515 or the amino acid of the position 516 serves as the C-terminus amino acid, and it is more preferred that the amino acid of the position 516 serves as the C-terminus amino acid. Further, there is also another embodiment in which the amino acid of the position 514 serves as the C-terminus amino acid, which is a preferred embodiment. Concerning the modification, diversity and the like described above, the same shall apply to a DNA having the nucleotide sequence of SEQ ID NO: 12.

The thrombomodulin obtained by the method described above may be a mixture of peptides having diversity in the N-terminus and C-terminus amino acids. Specific examples include a mixture of peptides having the sequences of the positions 19 to 516, positions 19 to 515, positions 19 to 514, positions 17 to 516, positions 17 to 515, and positions 17 to 514 in SEQ ID NO: 9.

Highly-purified soluble thrombomodulin in which contamination of HCP is reduced is provided by the present invention.

Examples of the highly-purified soluble thrombomodulin of this embodiment include highly-purified soluble thrombomodulin that does not substantially contain any protein other than soluble thrombomodulin. Specifically, an example includes a soluble thrombomodulin not substantially containing HCP, for example. Preferably, an example includes a soluble thrombomodulin not substantially containing HCP, mouse IgG, and bovine serum proteins.

The highly-purified soluble thrombomodulin of this embodiment contains no proteins originated from human.

The content of HCP is not particularly limited so far that the soluble thrombomodulin is in a state that it does not substantially contain HCP. The content is preferably a ratio of HCP being less than 10 ng, more preferably less than 8 ng, still more preferably less than 7 ng, further more preferably less than 6 ng, most preferably less than 5 ng per 10,000 U of soluble thrombomodulin. The highly-purified soluble thrombomodulin of this embodiment is produced in a transformant cell obtained by transfecting a host cell with a DNA containing a nucleotide sequence encoding soluble thrombomodulin, and it is considered that even the product is purified as highly as possible, there still actually is a possibility of contamination of HCP in a trace amount and the like. A content of HCP as low as possible is preferred. An example of minimum content of HCP includes, for example, a ratio of 0.001 ng of HCP per 10,000 U of soluble thrombomodulin.

The content of mouse IgG is not particularly limited so far that the soluble thrombomodulin is in a state that it does not substantially contain mouse IgG. A ratio of less than 10 ng of mouse IgG is preferred, a ratio of less than 2 ng is more preferred, and the ratio of less than 0.6 ng is still more preferred per 10,000 U of soluble thrombomodulin.

The content of bovine serum proteins is not particularly limited so far that the soluble thrombomodulin is in a state that it does not substantially contain bovine serum proteins. A ratio of less than 10 ng of bovine serum proteins is preferred, a ratio of less than 2 ng is more preferred, and a ratio of less than 0.6 ng is still more preferred per 10,000 U of soluble thrombomodulin. Concentrations of these proteins are preferably measured by ELISA, and the measurement can be performed by referring to Biochemical Experimental Methods, Vol. 11, Enzyme Immunoassay, Tokyo Kagaku Dojin (1992), and the like.

As for thrombomodulin purity of soluble thrombomodulin based on the total proteins in the highly-purified soluble thrombomodulin of this embodiment, the purity is preferably 99% or higher, more preferably 99.5% or higher, still more preferably 99.7% or higher, most preferably 99.9% or higher according to HPLC method. A type of the chromatography used in the HPLC method is not limited so far that purity of the soluble thrombomodulin can be measured. Examples include gel filtration liquid chromatography, ion exchange liquid chromatography, reverse phase liquid chromatography, and the like, and gel filtration liquid chromatography is preferred. When gel filtration liquid chromatography is used, the column to be used may be chosen depending on the molecular weight of the soluble thrombomodulin. An example includes, for example, a method of development by using a phosphate buffer of pH 7.3 using TOSOH TSKgel G3000SWXL (TOSOH, Japan). The test may be performed according to the description in Japanese Pharmacopoeia, Liquid Chromatography <2.01>.

In the highly-purified soluble thrombomodulin of this embodiment, DNA components originated from the host is preferably at a ratio of less than 2 ng, more preferably less than 0.2 ng, still more preferably less than 0.02 ng per 10,000 U of soluble thrombomodulin. Amount of DNAs can be easily measured by using Threshold System (Molecular Devices, U.S.A.).

A form of the highly-purified soluble thrombomodulin of this embodiment is not particularly limited so far that the content of HCP is within a ratio of less than 10 ng per 10,000 U of soluble thrombomodulin, and it can exist in the form of a solution or powder. The product preferably exists in the form of a solution. There is also another embodiment in which the product exists in the form of powder, which is a preferred embodiment. As for a concentration in the form of a solution, an upper limit is preferably 100 mg/mL or lower, more preferably 60 mg/mL or lower, still more preferably 30 mg/mL or lower, most preferably 15 mg/mL or lower, and lower limit is preferably 2 mg/mL or higher, more preferably 4 mg/mL or higher, still more preferably 6 mg/mL or higher, further more preferably 8 mg/mL or higher, most preferably 10 mg/mL or higher. Further, when the product exists in the form of a powder, a preferred example includes the form of a lyophilized powder. Such lyophilized product can be obtained by referring to the method described in WO03/061687.

The highly-purified soluble thrombomodulin of this embodiment can be obtained so as not to substantially contain endotoxins. The endotoxin content may preferably be less than 1 endotoxin unit (EU), more preferably less than 0.2 EU, still more preferably less than 0.04 EU, per 10,000 U of soluble thrombomodulin. Amount of endotoxins can be measured in accordance with the descriptions in Japanese Pharmacopoeia, General Test Procedures, Endotoxin Test Method <4.01>. Further, the highly-purified soluble thrombomodulin of this embodiment can be obtained in a state that it does not contain any substances harmful to living bodies such as TFA and almost in a sterile state, and accordingly, can be used as a material for pharmaceutical products.

The highly-purified soluble thrombomodulin of this embodiment in which contamination of HCP is reduced can be obtained by bringing a solution containing soluble thrombomodulin into contact with nylon and/or polyethersulfone. It is preferable to use nylon. There is also another embodiment in which it is preferable to use polyethersulfone.

Examples of nylon with which a solution containing the soluble thrombomodulin of this embodiment is brought into contact include, for example, polyamides containing an aliphatic structure such as Nylon 6, Nylon 66, Nylon 46, and Nylon MXD 6. The type of nylon is not limited so far that the nylon can adsorb HCP. Nylon 6 is preferred. Nylon is available as, for example, Minisart NY sold by Sartorius. The form of nylon is not particularly limited so far that the nylon is in such a form that a solution can be contacted, such as those of membrane, nonwoven fabric, and beads. The nylon is preferably molded in the form of membrane and used as a filtration membrane. In this embodiment, a pore diameter of the filtration membrane is not limited so far that the diameter allows HCP to pass through the membrane, for example, 0.01 to 10 μm, preferably 0.1 to 1 μm, more preferably 0.01 to 0.06 μm. The volume of the solution containing the soluble thrombomodulin to be contacted with nylon can be easily determined by bringing a part of the solution into contact with a small amount of nylon beforehand to evaluate the HCP-removing ability thereof.

The highly-purified soluble thrombomodulin of this embodiment can be prepared with confirming that the HCP content in the solution obtained by bringing a soluble thrombomodulin-containing solution containing HCP into contact with nylon is in a ratio of less than 10 ng of HCP per 10,000 U of soluble thrombomodulin, and when the HCP content becomes 10 ng or higher per 10,000 U of soluble thrombomodulin, collection of highly-purified soluble thrombomodulin can be terminated, or after the used nylon is changed to fresh nylon, the collection of highly-purified soluble thrombomodulin may be restarted. As for examples of the relation between the amount of HCP and the area of nylon, examples where a nylon is in the form of filtration membrane for example include an upper limit of the area of the membrane being 50 $m^2$ or smaller, preferably 5 $m^2$ or smaller, more preferably 0.5 $m^2$ or smaller, still more preferably 0.1 $m^2$ or smaller, and preferably a lower limit being 0.01 m² or larger, more preferably 0.02 m² or larger, still more preferably 0.03 m² or larger, per 1 mg of HCP. It is important to determine the membrane area depending on the amount of HCP desired to be reduced.

The polyethersulfone with which a solution containing the soluble thrombomodulin of this embodiment is brought into contact is available as, for example, Minisart High-Flow sold by Sartorius. The form of polyethersulfone is not particularly limited so far that it is in such a form that a solution can be contacted, such as those of membrane, nonwoven fabric, and beads. Polyethersulfone is preferably molded in the form of membrane and used as a filtration membrane. In this embodiment, a pore diameter of the filtration membrane is not limited so far that the diameter allows HCP to pass through the membrane, for example, 0.01 to 10 μm, preferably 0.1 to 1 μm, more preferably 0.01 to 0.06 μm. The volume of the solution containing the soluble thrombomodulin to be contacted with polyethersulfone can be easily determined by bringing a part of the solution into contact with a small amount of polyethersulfone beforehand to evaluate the HCP-removing ability thereof.

The highly-purified soluble thrombomodulin of this embodiment can be collected with confirming that the HCP content in the solution obtained by bringing a soluble thrombomodulin-containing solution containing HCP into contact with polyethersulfone is in a ratio of less than 10 ng per 10,000 U of soluble thrombomodulin, and when the HCP content becomes 10 ng or higher per 10,000 U of soluble thrombomodulin, collection of highly-purified soluble thrombomodulin can be terminated, or after the used polyethersulfone is changed to fresh polyethersulfone, the collection of highly-purified soluble thrombomodulin may be restarted. As for examples of the relation between the amount of HCP and the area of polyethersulfone, examples where a polyethersulfone is in the form of filtration membrane for example include an upper limit of the area of the membrane being 50 m² or smaller, preferably 5 m² or smaller, more preferably 0.5 m² or smaller, still more preferably 0.1 m² or smaller, and preferably a lower limit being 0.01 m² or larger, more preferably 0.02 m² or larger, still more preferably 0.03 m² or larger, per 1 mg of HCP. It is important to determine the membrane area depending on the amount of HCP desired to be reduced.

The production process of the highly-purified soluble thrombomodulin of this embodiment in which contamination of HCP is reduced is not particularly limited, so far that the process comprises the step of bringing a solution containing soluble thrombomodulin into contact with nylon and/or polyethersulfone so that the HCP content can be in a ratio of less than 10 ng per 10,000 U of soluble thrombomodulin.

An example includes the following production process:
A production process comprising the steps of (a) to (g), and the step of bringing a solution containing soluble thrombomodulin into contact with nylon and/or polyethersulfone
(a) the step of culturing a transformant cell and collecting culture medium (production solution),
(b) the step of filtering the production solution to obtain a filtered production solution,
(c) the step of applying the filtered production solution to anion exchange column chromatography to obtain a roughly purified solution,
(d) the step of applying the roughly purified solution to affinity column chromatography using a column carrying anti-thrombomodulin monoclonal antibody to obtain a purified solution 1,
(e) the step of applying the purified solution 1 to cation exchange column chromatography to obtain a purified solution 2,
(f) the step of applying the concentrated purified solution 2 to gel filtration column chromatography, and concentrating the eluate to obtain a purified solution 3, and
(g) the step of filtering the purified solution 3 with a virus-removing membrane and a sterile filtration membrane.

In the aforementioned production process, the step of bringing a solution containing soluble thrombomodulin into contact with nylon and/or polyethersulfone may be included in any one of or two or more of the steps (b) to (g). It is preferred that the process includes any one of or two or more of the steps (d) to (g). In order to efficiently remove HCP, it is extremely preferable to perform the step of bringing the solution into contact with nylon and/or polyethersulfone after the final step of the production process, i.e., the step (g).

Further, in order to completely obviate contamination of bovine serum proteins, it is more preferred that the culture of the transformant cell in the step (a) is performed as serum-free culture.

Examples of the production process of the highly-purified soluble thrombomodulin of this embodiment in which contamination of HCP is reduced also include the following production process:
A production process comprising the steps of (a) to (g), and the step of bringing a solution containing soluble thrombomodulin into contact with nylon and/or polyethersulfone:
(a) the step of culturing a transformant cell and collecting culture medium (production solution),
(b) the step of filtering the production solution to obtain a filtered production solution,
(c) the step of applying the filtered production solution to anion exchange column chromatography to obtain a roughly purified solution 1,
(d) the step of applying the roughly purified solution to hydrophobic column chromatography to obtain a roughly purified solution 2,
(e) the step of applying the roughly purified solution 2 to affinity column chromatography using a column carrying anti-thrombomodulin monoclonal antibody to obtain a purified solution 1,
(f) the step of applying the concentrated purified solution 1 to gel filtration column chromatography to obtain a purified solution 2, and
(g) the step of filtering the purified solution 2 with a sterile filtration membrane.

In the aforementioned production process, the step of bringing a solution containing soluble thrombomodulin into contact with nylon and/or polyethersulfone may be included in any one of or two or more of the steps (b) to (g). It is preferable that said step is included in any one of or two or more of the steps (e) to (g). In order to efficiently remove HCP, it may be preferable to perform the step of bringing the solution into contact with nylon and/or polyethersulfone after the final step of the production process, i.e., the step (g).

Further, in order to completely obviate contamination of bovine serum proteins, it is more preferred that the culture of the transformant cell in the step (a) is performed as serum-free culture.

The highly-purified soluble thrombomodulin of this embodiment can be prepared with confirming that the HCP content in the solution obtained by bringing a soluble thrombomodulin-containing solution containing HCP into contact with nylon and/or polyethersulfone is in a ratio of less than 10 ng per 10,000 U of soluble thrombomodulin, and when the HCP content becomes 10 ng or larger per 10,000 U of soluble thrombomodulin, the preparation of highly-purified soluble thrombomodulin may be terminated, or after the used nylon and/or polyethersulfone is changed to fresh nylon and/or polyethersulfone, the preparation of highly-purified soluble thrombomodulin may be restarted. As described above, the production process of the highly-purified soluble thrombomodulin of this embodiment in which contamination of HCP is reduced is not particularly limited so far that the process comprises the step of bringing a solution containing soluble thrombomodulin into contact with nylon and/or polyethersulfone, and HCP content becomes in a ratio of less than 10 ng per 10,000 U of soluble thrombomodulin. More specifically, a purification step may be performed after the step of bringing the solution into contact with nylon and/or polyethersulfone, and as a result, it is sufficient that highly-purified soluble thrombomodulin having an HCP content being in a ratio of less than 10 ng of HCP per 10,000 U of soluble thrombomodulin can be obtained.

Examples of the purification step that may be performed after the step of bringing the solution into contact with nylon and/or polyethersulfone include steps of performing column chromatography such as anion exchange column chromatography, affinity column chromatography, cation exchange column chromatography, gel filtration column chromatography, and hydrophobic column chromatography, membrane filtration such as membrane concentration, virus removing, and sterile filtration, or a combination of two or more of these treatments. A step of performing cation exchange column chromatography, gel filtration column chromatography, membrane concentration, virus removing, sterile filtration, or a combination of two or more of these treatments is preferred. It may be preferable to perform cation exchange column chromatography, gel filtration column chromatography, membrane concentration, virus removing, and sterile filtration after the step of bringing the solution into contact with nylon and/or polyethersulfone. As a more preferred example, the purification step comprising cation exchange column chromatography, gel filtration column chromatography, membrane concentration, virus removing, and sterile filtration may be performed by performing cation exchange column chromatography, membrane concentration, gel filtration column chromatography, membrane concentration, virus removing, and sterile filtration in this order, after the step of bringing the solution into contact with nylon and/or polyethersulfone. Examples of the material used for the cation exchange column chromatography include SP Sepharose Fast Flow, DEAE Sepharose Fast Flow, Capto S, Capto DEAE (GE Healthcare), S HyperCel (Pall), and TOYOPEARL GigaCap S-650 (TOSOH), and SP Sepharose Fast Flow is preferred. Examples of the concentration membrane include MICROZA OF (Asahi Kasei Chemicals), Kvick Flow 10 KD (GE Healthcare), and Pellicon 2 (Millipore), and MICROZA UF is preferred. Examples of the material used for the gel filtration column chromatography include Sephacryl S-300 HR, Superose 12 pg (GE Healthcare), and TOYOPEARL HW (TOSOH), and Sephacryl S-300 HR is preferred. Examples of the virus-removing membrane include PLANOVA 15N (Asahi Kasei Medical), Biresolve NFP (Millipore), and Ultipor VF (Pall), and PLANOVA 15N is preferred. Examples of the sterile filtration membrane include Millipak, Millidisk (Millipore), Supor EVA (Pall), and Sartopore 2 (Sartorius Stedim), and Millipak is preferred.

As described above, the highly-purified soluble thrombomodulin of this embodiment obtained by bringing a solution containing soluble thrombomodulin into contact with nylon and/or polyethersulfone contains HCP being in a ratio of less than 10 ng of HCP per 10,000 U of soluble thrombomodulin.

One U of the soluble thrombomodulin of this embodiment is defined as an amount that can generate 0.1 μmol of p-nitroaniline per 1 minute in the APC assay using activation of Protein C as an index, and can be measured by the method comprising the following steps according to the method described in Biologicals, 30, 69-76 (2002):
(a) the step of adding human thrombin to a test solution containing soluble thrombomodulin, and warming the mixture,
(b) the step of adding human Protein C, and warming the mixture,
(c) the step of adding heparin-antithrombin III, and warming the mixture,
(d) the step of adding a synthetic substrate S-2366 (pyroGlu-Pro-Arg-pNA-HCl), and warming the mixture,
(e) the step of adding acetic acid to terminate the substrate cleaving reaction,
(f) the step of measuring absorbance at 405 nm, and
(g) the step of determining activity of the soluble thrombomodulin-containing test solution in accordance with the following equation:

$$\text{Activity (U/mL)} = [(A_{sample} - A_{blank}) \times V_1]/(M \times T \times k \times V_2) \times \text{Dilution time of sample} \quad \text{[Equation 1]}$$

$A_{sample}$: Absorbance of sample solution
$A_{blank}$: Absorbance of blank (water)
M: Molar absorption coefficient of p-nitroaniline: $9.6 \times 10^{-3}$ [1/μM]
$V_1$: Volume at the time of spectrometry (L)
$V_2$: Volume of sample solution (mL)
T: Substrate cleaving reaction time (minute)
k: Molar number of p-nitroaniline released by activated Protein C generated by 1 U of thrombomodulin 0.1 (μmol/minute/U)

The highly-purified soluble thrombomodulin of this embodiment has the activity of, for example, 3,000 U, preferably 4,000 to 9,000 U, more preferably 5,000 to 8,000 U, still more preferably 6,000 to 7,000 U, per 1 mg of the protein. Concentration of the protein can be measured in accordance with a known method for measuring protein concentration by using bovine serum albumin as a standard sample. Examples of the method include, for example, Lowry method, Bradford method, BCA method, and the like.

The HCP content of the highly-purified soluble thrombomodulin of this embodiment is measured by a method comprising at least the following steps:
(a) the step of preparing host cell-originated proteins from culture supernatant obtained by carrying out serum-free culture of a transformant cell obtained by transfecting a host cell with a DNA containing a nucleotide sequence encoding soluble thrombomodulin, or the host cell,
(b) the step of purifying an anti-host cell-originated protein antibody from antiserum obtained by sensitizing a rabbit with the host cell-originated proteins obtained in (a) mentioned above,
the step of constructing a measurement system comprising:
(c1) the step of adsorbing the anti-host cell-originated protein antibody obtained in (b) mentioned above to a solid phase,
(c2-1) the step of bringing a soluble thrombomodulin-containing test solution suspected to be contaminated with the host cell-originated proteins into contact with the solid phase to which the anti-host cell-originated protein antibody is adsorbed,
(c3) the step of adding a biotinylated anti-host cell-originated protein antibody to the solid phase, (c4) the step of adding a solution of avidinylated peroxidase to the solid phase, (c5) the step of adding an enzyme substrate solution to allow color development, and (c6) the step of terminating the color development and measuring absorbance, (d) the step of measuring concentration of the host cell-originated proteins in the soluble thrombomodulin-containing test solution suspected to be contaminated with the host cell-originated proteins in the aforementioned measurement system, and determining whether the concentration of the host cell-originated proteins in the soluble thrombomodulin-containing test solution is within a range that enables quantification of the proteins in the aforementioned measurement system, which range is confirmed beforehand by performing measurement using a solution of the host cell-originated proteins of a known concentration in the aforementioned measurement system, (e-1) the step of determining the concentration of the host cell-originated proteins in the soluble thrombomodulin-containing test solution suspected to be contaminated with the host cell-originated proteins as the concentration of the host cell-originated proteins in the solution, when the concentration is determined to be within the range that enables the quantification in (d) mentioned above, (e-2-1) the step of concentrating or diluting the soluble thrombomodulin-containing test solution suspected to be contaminated with the host cell-originated proteins, if desired, to make the concentration of the host cell-originated proteins to be a measurable concentration within the range that enables the quantification in the aforementioned measurement system, when the concentration of the host cell-originated proteins is determined to be not within the range that enables the quantification in (d) mentioned above, and recording the concentration ratio or dilution ratio, (e-2-2) the step of measuring the host cell-originated protein concentration in the soluble thrombomodulin-containing test solution concentrated or diluted in (e-2-1) mentioned above in a measurement system corresponding to the measurement system represented by the steps of (c1) to (c6) mentioned above in which (c2-1) is replaced with (c2-2) mentioned below, and obtaining the host cell-originated protein concentration with taking the concentration ratio or dilution ratio into consideration, (c2-2) the step of bringing the soluble thrombomodulin-containing test solution concentrated or diluted, if necessary, into contact with the solid phase to which the anti-host cell-originated protein antibody is adsorbed, and the step of bringing a solution containing the host cell-originated proteins of a known concentration into contact with the solid phase to which the anti-host cell-originated protein antibody is adsorbed, and (f) the step of calculating ratio of the host cell-originated protein concentration obtained in (e-1) or (e-2-2) based on APC activity of thrombomodulin per unit volume of the soluble thrombomodulin-containing test solution measured separately.

In this specification, HCP means proteins originated from the host cells used for preparing gene recombinant cells that produce soluble thrombomodulin, and does not mean to include soluble thrombomodulin. HCP can be prepared from culture supernatant obtained by culturing host cells of the same type as those of the cells used for the transfection with a DNA containing the nucleotide sequence encoding thrombomodulin. In the case of CHO cell, for example, the term of host cell of the same type means a concept encompassing cells of strains classified into CHO cells, such as those of the cell lines CHO-K1 (ATCC No. CCL-61), CHO-S (Invitrogen, U.S.A., Catalog No. 11619.012), CHO-DXB11, and CHO-DG44 (Invitrogen, U.S.A., Catalog No. 12610-010), and the preparation may be performed by using any of cell lines classified into CHO cells. As for the CHO cell, it is preferable to use cells of the cell line DXB11 or CHO-K1, more preferably cells of the cell line DXB11, as the host cell of the same type. There is also another embodiment in which it is preferable to use cells of the cell line CHO-K1.

HCP means proteins originated from the host cells used for preparing the gene recombinant cells that produce soluble thrombomodulin, and is defined to be measurable by the method including at least the aforementioned steps (a) to (f). Examples of constituents of HCP include, as shown in Test Example 6, histone H2B (Biochimie, 61 (1), 61-69 (1979)).

Further, when preparation is carried out from the culture supernatant obtained by culturing the transformant cell obtained by transfecting a host cell of the same type with a DNA containing a nucleotide sequence encoding thrombomodulin, the culture supernatant can be applied to an antibody column using an antibody that specifically binds to thrombomodulin as the ligand, and a non-adsorbed fraction can be collected. After it is confirmed that the APC activity of thrombomodulin is not detected in this non-adsorbed fraction, the fraction can be used as HCP. HCP is preferably concentrated by using an ultrafiltration membrane, as required. In addition, in order to avoid contamination of other proteins, the medium used for culturing the host cell or the transformant cell is preferably a serum-free medium, and it is more preferred that the serum-free medium is a protein-free medium. For the purification of the anti-HCP antibody from an anti-HCP antiserum obtained by sensitizing a rabbit with HCP, column chromatography can be used, and for example, a combination of ammonium sulfate salting-out and column chromatography can be used. For the column chromatography for the purification of the anti-HCP antibody, it is preferable to use a Protein A column. There is also another embodiment in which, when a transformant cell obtained by transfecting a host cell with a DNA containing a nucleotide sequence encoding thrombomodulin is used for the preparation of HCP, it is preferred that a thrombomodulin column is used for purification of the anti-HCP antibody after the purification with a Protein A column, and the non-adsorbed fraction is collected and used as the anti-HCP antibody.

When an HCP concentration measurement system is constructed, it is necessary to clarify the quantifiable range thereof, and the quantifiable range is not limited so far that an HCP content of less than 10 ng of HCP per 10,000 U of thrombomodulin can be measured. It is more preferable that a lower concentration can be measured. The quantifiable range is defined to be, for example, 100 ng/mL or higher, preferably 50 ng/mL or higher, more preferably 25 ng/mL or higher, and for example, 500 ng/mL or lower.

When the test solution is concentrated, it can be concentrated by a usual protein concentration method, and the method is not particularly limited. However, it is preferably concentrated with an ultrafiltration membrane. Further, there is also another embodiment in which it is preferable to concentrate the test solution by lyophilizing the solution, and then dissolving the product with a small volume of water or buffer. Components other than HCP are also concentrated by the concentration and may affect the HCP measurement system. Accordingly, it is necessary to concentrate the test solution in such a degree that the HCP measurement system is not affected. For example, upper limit of the concentration of the soluble thrombomodulin-containing test solution not affecting the HCP measurement system is, for example, 5 mg/mL.

The HCP content per 10,000 U of thrombomodulin is calculated in accordance with the following equation.

$$a/b \times 10{,}000$$

a: HCP content per 1 mL of sample (ng/mL)
b: APC activity of thrombomodulin per 1 mL of sample (U/mL)

The highly-purified soluble thrombomodulin of this embodiment promotes the activation of Protein C by thrombin to provide generation of a large amount of active Protein C that has an anti-blood coagulation action and a thrombolysis action. Therefore, the highly-purified soluble thrombomodulin of this embodiment greatly contributes to anti-blood coagulation and thrombolysis in a living body. The highly-purified soluble thrombomodulin of this embodiment has an anti-blood coagulation action, a platelet aggregation inhibition action, and a thrombolysis action. Accordingly, the product can be used for a pharmaceutical composition for controlling blood coagulation, or controlling platelet aggregation. Specifically, it can be used for prophylactic and therapeutic treatments of diseases including, for example, myocardial infarction, thrombosis, embolism, peripheral vessel obstruction, obstructive arteriosclerosis, disseminated intravascular coagulation (DIC), angina pectoris, transient cerebral ischemic attack, toxemia of pregnancy, and the like.

When the pharmaceutical composition of this embodiment is prepared, the highly-purified soluble thrombomodulin of this embodiment and a pharmaceutically acceptable carrier can be mixed. More specifically, a pharmaceutical composition suitable for effective administration to patients can be prepared by mixing the highly-purified soluble thrombomodulin of this embodiment in an amount effective for a prophylactic or therapeutic treatment of any of the diseases mentioned above with an appropriate amount of carrier. As the pharmaceutical composition of this embodiment, a lyophilized preparation can be preferably prepared. Further, the pharmaceutical composition of this embodiment is preferably used as a preparation for intravascular injection. The composition can also be preferably prepared as a preparation for intravenous infusion. A lyophilized preparation can be prepared by referring to the method described in WO03/061687.

When the composition is used as an injection, the aforementioned carrier is preferably a carrier that can be administered as a pharmaceutical, and can be dissolved in physiological saline or glucose injection. Examples of the carrier include one or more selected from the group consisting of sucrose, purified gelatin, albumin, mannitol, glucose, and sodium chloride. For example, a pH adjustor consisting of any of various mineral salts, and the like are also preferably added. In such a case, the whole pharmaceutical composition as a combination with the highly-purified soluble thrombomodulin of this embodiment is soluble, and can be finely lyophilized, and thus such a composition is preferred. Further, in this embodiment, it is also preferred that the aforementioned carrier is glycerol. The aforementioned carrier is preferably added at the time of preparing the composition. The carrier may also be added when the composition is dissolved before use.

A dose of the highly-purified soluble thrombomodulin of this embodiment for one time of administration to an adult may change depending on age, sex, body weight, symptoms, and the like. The doses may generally be about 0.1 to 200 mg, and may be administered, for example, once or several times, as required, per day by intravascular injection, preferably intravenous drip infusion. The pharmaceutical composition of this embodiment may also be administered so that a dose can be 0.1 to 200 mg of the soluble thrombomodulin as the active ingredient, for example, once or several times, as required, per day by intravascular injection, preferably intravenous drip infusion.

EXAMPLES

The present invention will be more specifically explained with reference to the following examples. However, the scope of the present invention is not limited at all by these.

Reference Example 1

Method for Measuring APC Activity of Thrombomodulin

According to the description of Biologicals, 30, 69-76 (2002), the APC activity of thrombomodulin is measured on the basis of activation of Protein C as an index.

A 20 mM calcium chloride solution (75 μL) is added with 25 μL of a sample solution diluted with a Tris-imidazole buffer containing 0.05% polysorbate 20, the mixture is cooled on ice, and then added with 25 μL of a 40 U/mL solution of human thrombin (Sigma, U.S.A.), and the mixture is stirred and warmed at 37° C. Ten minutes after the addition of the human thrombin solution, the mixture was added with 25 μL of a 12 U/mL solution of human Protein C (Enzyme Research, U.S.A.), and the mixture was stirred and warmed at 37° C. Ten minutes after the addition of the human Protein C solution, the mixture was added with 100 μL of a heparin-antithrombin III solution, and the mixture was stirred and warmed at 37° C. Ten minutes after the addition of the heparin-antithrombin III solution, the mixture was added with 250 μL of a synthetic substrate S-2366 (ChromoGenics, Sweden) solution warmed at 37° C. beforehand, and the mixture is stirred and warmed at 37° C. Ten minutes after the addition of the substrate solution, the mixture was added with 1.5 mL of 50% acetic acid, the mixture is stirred, and absorbance of the mixture is measured at 405 nm by using water as a blank.

The APC activity of thrombomodulin is calculated in accordance with the following equation. One U of thrombomodulin is defined as an amount that can generate 0.1 μmol of p-nitroaniline per 1 minute.

$$\text{Activity (U/mL)} = [(A_{sample} - A_{blank}) \times V_1]/(M \times T \times k \times V_2) \times \text{Dilution time of sample} \quad \text{[Equation 2]}$$

$A_{sample}$: Absorbance of sample solution
$A_{blank}$: Absorbance of blank (water)
M: Molar absorption coefficient of p-nitroaniline: $9.6 \times 10^{-3}$ [1/μM]
$V_1$: Volume at the time of spectrometry: $2.0 \times 10^{-3}$ (L)
$V_2$: Volume of sample solution: 0.025 (mL)
T: Substrate cleaving reaction time: 10 (minute)
k: Molar number of p-nitroaniline released by activated Protein C generated with 1 U of thrombomodulin 0.1 (μmol/minute/U)

The reagents are as follows.
<Tris-Imidazole Buffer>
Solution B (100 mL) is added with Solution A, and the mixture is adjusted to pH 8.4, and diluted 10 times with water.
Solution A: 2-Amino-2-hydroxymethyl-1,3-propanediol (3.03 g) and imidazole (1.70 g) are dissolved in 1 M hydrochloric acid (50 mL), the solution was added with water to a volume of 100 mL, and sodium chloride (11.7 g) is added to the solution and dissolved.

Solution B: 2-Amino-2-hydroxymethyl-1,3-propanediol (4.04 g), imidazole (2.27 g), and sodium chloride (1.95 g) are dissolved in water to obtain a volume of 100 mL, and sodium chloride (11.7 g) is added to the solution and dissolved.

<20 mM Calcium Chloride Solution>

A 60 mM calcium chloride solution (1 mL) is added with a Tris-imidazole buffer (2 mL).

<Heparin-Antithrombin III Solution>

An antithrombin III solution (2 U/mL, 7.5 µL, Mitsubishi Pharma, Japan), a Tris-imidazole buffer (42.5 µL), and a 30 U/mL heparin solution (50 µL, Mochida Pharmaceutical, Japan) are mixed by shaking. This solution is prepared before use, and cooled on ice until just before use.

Reference Example 2

Method for Measuring HCP Concentration

Serum-free culture of gene recombinant CHO cells introduced with the thrombomodulin gene is performed. The culture supernatant is applied on an anti-thrombomodulin antibody column to obtain a non-adsorbed fraction. According to the description of Reference Example 1, the APC activity of thrombomodulin in this non-adsorbed fraction is measured to confirm that the activity is not detected, then the fraction is concentrated with an ultrafiltration membrane, and the concentrate is used as HCP. Anti-HCP antiserum obtained by sensitizing a rabbit with HCP as an antigen is purified by ammonium sulfate salting-out and with a Protein A column, and then applied on an affinity column using thrombomodulin as the ligand to obtain a non-adsorbed fraction. As described above, a rabbit anti-HCP antibody that does not recognize thrombomodulin is obtained.

A sample solution is obtained by dilution with PBS containing 0.05% polysorbate 80 so that expected HCP concentration becomes 0 to 500 ng/mL. When the HCP concentration of a sample solution is low, the solution is concentrated to an appropriate concentration by using an ultrafiltration membrane or the like. Separately, HCP is added with PBS containing 0.05% polysorbate 80 to prepare eight kinds of solutions containing 500, 400, 300, 200, 100, 50, 25, and 0 ng of HCP in 1 mL as standard solutions.

A 25 µg/mL rabbit anti-HCP antibody solution diluted with a sodium carbonate buffer is added to a 96-well polystyrene plate in a volume of 100 µL per well, and the plate is left standing at 25° C. for about 2 hours. Then, each well is washed 5 times with 250 µL of PBS containing 0.05% polysorbate 80, PBS containing 1% gelatin (200 µL) is added to each well, and the plate is left standing at 25° C. for about 1 hour. Each well is washed 5 times with 250 µL of PBS containing 0.05% polysorbate 80, then a sample solution and the standard solutions (100 µL) are added to the wells, and the plate is left standing at 25° C. for about 16 hours. Then, each well is washed 5 times with 250 µL of PBS containing 0.05% polysorbate 80, then a biotinylated rabbit anti-HCP antibody solution (100 µL) is added to each well, and the plate is left standing at 25° C. for about 2 hours. Each well is washed 5 times with 250 µL of PBS containing 0.05% polysorbate 80, then an avidin-peroxidase solution (100 µL) is added to each well, and the plate is left standing at 25° C. for about 2 hours. Each well is washed 5 times with 250 µL of PBS containing 0.05% polysorbate 80, then an enzyme substrate solution (100 µL) is added to each well, and the plate is left standing at room temperature in a dark place. When a color is appropriately developed, 50 µL of 25% sulfuric acid is added to each well to terminate the reaction, and absorbance of the mixture is measured at 492 nm with an absorptiometer for 96-well plates (Tecan Japan, Japan). By using a calibration curve prepared with the standard solutions, HCP content in the sample (1 mL) is calculated. The measurement limit of this measurement method is, for example, 25 ng/mL. In accordance with the following equation, HCP content per 10,000 U of thrombomodulin is calculated, as required.

$$\text{HCP content per 10,000 U of thrombomodulin (ng/10,000 U)} = a/b \times 10{,}000$$

a: HCP content per 1 mL of sample (ng/mL)
b: APC activity of thrombomodulin per 1 mL of sample (U/mL)

The reagents are as follows.

<Sodium Carbonate Buffer>

Anhydrous sodium carbonate (0.16 g), and sodium hydrogencarbonate (0.29 g) are added to water and dissolved to obtain a volume of 100 mL.

<Avidin-Peroxidase Solution>

A stock solution of horseradish peroxidase bound with avidin D (Vector Laboratories, U.S.A.) is diluted about 30,000 times with PBS containing 0.05% polysorbate 80.

<Enzyme Substrate Solution>

Ortho-phenylenediamine dihydrochloride (10 mg) is added to 20 mL of a citrate/phosphate buffer (citric acid monohydrate (2.56 g) and disodium hydrogenphosphate dodecahydrate (9.12 g) are dissolved in water to obtain a volume of 500 mL) and dissolved, and aqueous hydrogen peroxide (10 µL) is added immediately before use.

Reference Example 3

Method for Measuring Mouse IgG Concentration

Anti-mouse IgG antiserum obtained by sensitizing a rabbit with mouse IgG as an antigen is purified by ammonium sulfate salting-out and with a Protein A column to obtain a rabbit anti-mouse IgG antibody.

A sample solution is obtained by dilution with PBS containing 0.05% polysorbate 80 so that expected mouse IgG concentration becomes 0 to 25 ng/mL. When the IgG concentration of a sample solution is low, the solution is concentrated to an appropriate concentration by using an ultrafiltration membrane or the like. Separately, mouse IgG is added with PBS containing 0.05% polysorbate 80 to prepare eight kinds of solutions containing 25, 20, 15, 10, 5, 2.5, 1.25, 0.63, and 0 ng of IgG in 1 mL as standard solutions.

A 1.5 µg/mL rabbit anti-mouse IgG antibody solution diluted with a sodium carbonate buffer is added to a 96-well polystyrene plate in a volume of 100 µL per well, and the plate is left standing at 25° C. for about 2 hours. Then, each well is washed 5 times with 250 µL of PBS containing 0.05% polysorbate 80, PBS containing 1% gelatin (200 µL) is added to each well, and the plate is left standing at 25° C. for about 1 hour. Each well is washed 5 times with 250 µL of PBS containing 0.05% polysorbate 80, then a sample solution and the standard solutions (100 µL) are added to the wells, and the plate is left standing at 25° C. for about 16 hours. Then, each well is washed 5 times with 250 µL of PBS containing 0.05% polysorbate 80, and then a biotinylated rabbit anti-mouse IgG antibody solution (100 µL) is added to each well, and the plate is left standing at 25° C. for about 2 hours. Each well is washed 5 times with 250 µL of PBS containing 0.05% polysorbate 80, then an avidin-peroxidase solution (100 µL) is added to each well, and the plate is left standing at 25° C. for about 2 hours. Each well is washed 5 times with 250 µL of PBS containing 0.05% polysorbate 80, then an enzyme substrate solution (100 µL) is added to each well, and the plate is left standing at room temperature in a dark place. When a color is appropriately developed, 50 µL of 25% sulfuric acid is added to each well to terminate the reaction, and absorbance of the mixture is measured at 492 nm with an absorptiometer for 96-well plates (Tecan Japan, Japan). By using a calibration curve prepared with the standard solutions, mouse IgG content in the sample (1 mL) is calculated. The measurement limit of this measurement method is, for example, 0.63 ng/mL. In accordance with the following equation, mouse IgG content per 10,000 U of thrombomodulin is calculated, as required.

$$\text{Mouse IgG content per 10,000 U of thrombomodulin (ng/10,000 U)} = a/b \times 10,000$$

a: Mouse IgG content per 1 mL of sample (ng/mL)
b: APC activity of thrombomodulin per 1 mL of sample (U/mL)

The reagents are as follows.
<Sodium Carbonate Buffer>
Anhydrous sodium carbonate (0.16 g), and sodium hydrogencarbonate (0.29 g) are added to water and dissolved to obtain a volume of 100 mL
<Avidin-Peroxidase Solution>
A stock solution of horseradish peroxidase bound with avidin D (Vector Laboratories, U.S.A.) is diluted about 30,000 times with PBS containing 0.05% polysorbate 80.
<Enzyme Substrate Solution>
Ortho-phenylenediamine dihydrochloride (10 mg) is added to 20 mL of a citrate/phosphate buffer (citric acid monohydrate (2.56 g) and disodium hydrogenphosphate dodecahydrate (9.12 g) are dissolved in water to obtain a volume of 500 mL) and dissolved, and aqueous hydrogen peroxide (10 µL) is added immediately before use.

Reference Example 4

Method for Measuring Bovine Serum Protein Concentration

Anti-bovine serum protein antiserum obtained by sensitizing a rabbit with bovine serum as an antigen is purified by ammonium sulfate salting-out and with a Protein A column to obtain a rabbit anti-bovine serum protein antibody.

A sample solution is obtained by dilution with PBS containing 0.05% polysorbate 80 so that expected bovine serum protein concentration becomes 0 to 25 ng/mL. When the bovine serum protein concentration of a sample solution is low, the solution is concentrated to an appropriate concentration by using an ultrafiltration membrane or the like. Separately, bovine serum is added with PBS containing 0.05% polysorbate 80 to prepare eight kinds of solutions containing 25, 20, 15, 10, 5, 2.5, 1.25, and 0 ng of bovine serum proteins in 1 mL as standard solutions.

A 10 µg/mL rabbit anti-bovine serum protein antibody solution diluted with a sodium carbonate buffer is added to a 96-well polystyrene plate in a volume of 100 µL per well, and the plate is left standing at 25° C. for about 2 hours. Then, each well is washed 5 times with 250 µL of PBS containing 0.05% polysorbate 80, PBS containing 1% gelatin (200 µL) is added to each well, and the plate is left standing at 25° C. for about 1 hour. Each well is washed 5 times with 250 µL of PBS containing 0.05% polysorbate 80, then a sample solution and the standard solutions (100 µL) are added to the wells, and the plate is left standing at 25° C. for about 16 hours. Then, each well is washed 5 times with 250 µL of PBS containing 0.05% polysorbate 80, then a biotinylated rabbit anti-bovine serum protein antibody solution (100 µL) is added to each well, and the plate is left standing at 25° C. for about 2 hours. Each well is washed 5 times with 250 µL of PBS containing 0.05% polysorbate 80, then an avidin-peroxidase solution (100 µL) is added to each well, and the plate is left standing at 25° C. for about 2 hours. Each well is washed 5 times with 250 µL of PBS containing 0.05% polysorbate 80, then an enzyme substrate solution (100 µL) is added to each well, and the plate is left standing at room temperature in a dark place. When a color is appropriately developed, 50 µL of 25% sulfuric acid is added to each well to terminate the reaction, and absorbance of the mixture is measured at 492 nm with an absorptiometer for 96-well plates (Tecan Japan, Japan). By using a calibration curve prepared with the standard solutions, bovine serum protein content in the sample (1 mL) is calculated. The measurement limit of this measurement method is, for example, 1.25 ng/mL. In accordance with the following equation, bovine serum protein content per 10,000 U of thrombomodulin is calculated, as required.

$$\text{Bovine serum protein content per 10,000 U of thrombomodulin (ng/10,000 U)} = a/b \times 10,000$$

a: Bovine serum protein content per 1 mL of sample (ng/mL)
b: APC activity of thrombomodulin per 1 mL of sample (U/mL)

The reagents are as follows.
<Sodium Carbonate Buffer>
Anhydrous sodium carbonate (0.16 g), and sodium hydrogencarbonate (0.29 g) are added to water and dissolved to obtain a volume of 100 mL.
<Avidin-Peroxidase Solution>
A stock solution of horseradish peroxidase bound with avidin D (Vector Laboratories, U.S.A.) is diluted about 30,000 times with PBS containing 0.05% polysorbate 80.
<Enzyme Substrate Solution>
Ortho-phenylenediamine dihydrochloride (10 mg) is added to 20 mL of a citrate/phosphate buffer (citric acid monohydrate (2.56 g) and disodium hydrogenphosphate dodecahydrate (9.12 g) are dissolved in water to obtain a volume of 500 mL) and dissolved, and aqueous hydrogen peroxide (10 µL) is added immediately before use.

Comparative Example 1

Preparation of Soluble Thrombomodulin 1

A gene recombinant CHO cell into which a DNA encoding the amino acid sequence of SEQ ID NO: 9 was introduced was prepared by a genetic manipulation technique according to Japanese Patent Unexamined Publication No. 11-341990, Example 1, then inoculated into the DMEM medium (Invitrogen, U.S.A.) containing 150 mg/L of L-proline (Ajinomoto, Japan), 60 mg/L of kanamycin sulfate (Meiji Seika, Japan), 1 mg/L of tylosin tartrate (Mercian, Japan), and 10% bovine serum (HyClone, U.S.A.), and cultured at 37° C. in a $CO_2$ incubator. The cells obtained by centrifuging the culture medium were suspended in the DMEM medium (Invitrogen, U.S.A.) containing 150 mg/L of L-proline (Ajinomoto, Japan), 60 mg/L of kanamycin sulfate (Meiji Seika, Japan), 1 mg/L of tylosin tartrate (Mercian, Japan), 10% dimethyl sulfoxide (Merck, Germany), and 10% bovine serum (HyClone, U.S.A.), and the medium was dispensed into vials ($4 \times 10^7$ cells/vial), and cryopreserved in liquid nitrogen.

Cell culture was performed by using, as the base medium, the medium described in Japanese Patent Unexamined Publication No. 11-341990, Ingredient Table 2, provided that $NaHCO_3$ concentration was changed to 5,700 mg/L, and NaCl concentration was changed to 2,410 mg/L. Growth medium was obtained by adding 60 mg/L of kanamycin sulfate (Invitrogen, U.S.A.), 1 mg/L of tylosin tartrate (Sigma-Aldrich, U.S.A.), and 8% bovine serum (HyClone, U.S.A.) to the base medium, and used. Further, production medium was the same as the growth medium, provided that the serum concentration was changed to 3%.

The cells of one vial were thawed, inoculated into 100 mL of the growth medium, and cultured with stirring at 37° C. for 5 days by using a spinner flask in a $CO_2$ incubator. When the living cell density became $7.0 \times 10^5$ cells/mL or more, the entire volume of the culture medium was transferred to 0.9 L of the growth medium, and the cells were cultured with stirring at 37° C. for 5 days by using a spinner flask in a $CO_2$ incubator. When the living cell density became $7.0 \times 10^5$ cells/mL or more, the entire volume of the culture medium was transferred to 9 L of the growth medium, and the cells were cultured with stirring at 37° C., pH 7.2 and 50% of dissolved oxygen for 5 days by using a culture tank. When the living cell density became $7.0 \times 10^5$ cells/mL or more, the entire volume of the culture medium was transferred to 120 L of the growth medium, and the cells were cultured with stirring at 37° C., pH 7.2 and 50% of dissolved oxygen for 7 days by using a perfusion culture tank. When the living cell density became $7.0 \times 10^5$ cells/mL or more, perfusion culture was started, in which the production medium was continuously added, and the culture supernatant was continuously collected. The culture conditions consisted of 37° C., pH 7.2, dissolved oxygen: 50%, medium exchange: 130 to 200 L/day, and surface pressurization: 0 to 0.2 MPa. After the living cell density reached $7.5 \times 10^6$ cells/mL, the culture was further continued for 36 days, and the culture supernatant was collected as a production solution. The collected production solution was clarified by using filtration filters, SUPRAdisc II (Pall, U.S.A.) and Supor EBV (Pall, U.S.A.), and stored at 2 to 10° C. as a filtered production solution.

About 700 L of the filtered production solution was applied to a Q-Sepharose Fast Flow (GE Healthcare, U.S.A.) column (diameter: 63 cm, height: 25 cm) equilibrated with a 20 mM Tris-hydrochloric acid buffer (pH 7.7) containing 150 mM sodium chloride. Then, the column was washed with 6 column volumes (CV) of a 20 mM acetate buffer (pH 5.5) containing 180 mM sodium chloride, and further washed with a 20 mM Tris-hydrochloric acid buffer (pH 7.7) containing 180 mM sodium chloride until absorbance at 280 nm returned to the baseline. Elution was started with a 20 mM Tris-hydrochloric acid buffer (pH 7.7) containing 300 mM sodium chloride, and 0.5 column volume of the eluate from the start of the peak of absorbance at 280 nm was obtained as a roughly purified solution. The same operation was repeated 6 times to obtain 6 lots of the roughly purified solution. The operation was performed at a temperature of 2 to 10° C., and a chromatography flow rate of 109 L/hour.

An anti-thrombomodulin monoclonal antibody was prepared by using human lung-originated thrombomodulin as the antigen according to Japanese Patent Unexamined Publication No. 11-341990, Example 10, contacted and reacted with CNBr-activated Sepharose 4 Fast Flow (GE Healthcare, U.S.A.) to couple the anti-thrombomodulin monoclonal antibody and thereby prepare anti-thrombomodulin monoclonal antibody-bound Sepharose 4 Fast Flow, which was filled in a column to obtain a monoclonal antibody column. About 40 L of the roughly purified solution was applied to the monoclonal antibody column (diameter: 44 cm, height: 13 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The same operation was repeated 6 times to obtain 6 lots of the purified solution 1. The operation was performed at a temperature of 2 to 10° C., and a chromatography flow rate of 46 L/hour.

About 170 L of the purified solution 1 of the 6 lots was adjusted to pH 3.5 with a 1.0 M glycine-hydrochloric acid buffer (pH 2.0), and applied to an SP-Sepharose FF (GE Healthcare Bioscience, U.S.A.) column (diameter: 45 cm, height: 10 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 160 L/hour.

About 200 L of the purified solution 2 was concentrated to about 10 L by using an ultrafiltration membrane, Microza UF Module SIP-2013 (Asahi Kasei Chemicals, Japan), and then applied to a Sephacryl S-300 HR (GE Healthcare Bioscience, U.S.A.) column (diameter: 63 cm, height: 94 cm) equilibrated with a 20 mM phosphate buffer (pH 7.3) containing 50 mM sodium chloride. An elution peak with the maximum absorbance at 280 nm was separated, and concentrated to about 12 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 6.2 L/hour.

The purified solution 3 was passed through a virus-removing membrane, PLANOVA 15N (membrane area: 1 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a purified product of soluble thrombomodulin.

By performing the same operation, 3 lots (A1, A2, A3) of the purified product were obtained.

The APC activities of thrombomodulin of A1, A2, and A3 were 69000 U/mL, 68000 U/mL, and 72000 U/mL, respectively.

Soluble thrombomodulin concentrations in the solutions of A1, A2, and A3 were 10.5 mg/mL, 10.2 mg/mL, and 10.3 mg/mL, respectively.

Comparative Example 2

Preparation Of Soluble Thrombomodulin 2

The medium described in Japanese Patent Unexamined Publication No. 11-341990, Ingredient Table 2 was used as the base medium. Growth medium was obtained by adding 60 mg/L of kanamycin sulfate (Invitrogen, U.S.A.), 1 mg/L of tylosin tartrate (Sigma-Aldrich, U.S.A.), and 8% bovine serum (HyClone, U.S.A.) to the base medium, and used. Further, production medium was the same as the growth medium, provided that the serum concentration was changed to 4%.

The cells of one vial prepared in Comparative Example 1 were thawed, inoculated into 100 mL of the growth medium, and cultured with stirring at 37° C. for 3 days by using a spinner flask in a $CO_2$ incubator. When the living cell density became $5.0 \times 10^5$ cells/mL or more, the entire volume of the culture medium was transferred to 400 mL of the growth medium, and the cells were cultured with stirring at 37° C. for 3 days by using a spinner flask in a $CO_2$ incubator. When the living cell density became $5.0 \times 10^5$ cells/mL or more, the entire volume of the culture medium was transferred to 2 L of the growth medium, and the cells were cultured with stirring at 37° C. for 3 days by using a spherical bottle in a $CO_2$ incubator. When the living cell density became $5.0 \times 10^5$ cells/mL or more, the entire volume of the culture medium was transferred to 7.5 L of the growth medium, and the cells were cultured with stirring at 37° C. for 4 days by using a spherical bottle in a $CO_2$ incubator. When the living cell density became $5.0 \times 10^5$ cells/mL or more, perfusion culture was started, in which the production medium was continuously added, and the culture supernatant was continuously collected. The culture conditions consisted of 37° C., pH 7.2, dissolved oxygen: 50%, medium exchange: 10 L/day, and surface pressurization: 0 to 0.2 MPa. After the living cell density reached $7.5 \times 10^6$ cells/mL, the culture was further continued for 40 days, and the culture supernatant was collected as a production solution.

The collected production solution was clarified by using filtration filters having pore diameters of 0.7 μm and 0.22 μm (Pall, U.S.A.), and stored at 2 to 10° C. as a filtered production solution.

About 400 L of the filtered production solution was applied to a Q-Sepharose Fast Flow (GE Healthcare, U.S.A.) column (diameter: 44 cm, height: 26 cm) equilibrated with a 20 mM Tris-hydrochloric acid buffer (pH 7.4) containing 150 mM sodium chloride. Then, the column was washed with 6 CV of a 20 mM acetate buffer (pH 5.5) containing 180 mM sodium chloride, and further washed with a 20 mM Tris-hydrochloric acid buffer (pH 7.4) containing 180 mM sodium chloride until absorbance at 280 nm returned to the baseline. Elution was started with a 20 mM Tris-hydrochloric acid buffer (pH 7.4) containing 300 mM sodium chloride, and 0.5 column volume of the eluate from the start of the peak of absorbance at 280 nm was obtained as a roughly purified solution. The operation was performed at a temperature of 2 to 10° C., and a chromatography flow rate of 45 L/hour.

About 20 L of the roughly purified solution was applied to a monoclonal antibody column (diameter: 44 cm, height: 12 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The operation was performed at a temperature of 2 to 10° C., and a chromatography flow rate of 45 L/hour.

About 12 L of the purified solution 1 was adjusted to pH 3.5 with a 1.0 M glycine-hydrochloric acid buffer (pH 2.0), and applied to an SP-Sepharose FF (GE Healthcare Bioscience, U.S.A.) column (diameter: 14 cm, height: 13 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 15 L/hour.

About 16 L of the purified solution 2 was concentrated to about 1.2 L by using an ultrafiltration membrane, Microza UF Module SIP-1013 (Asahi Kasei Chemicals, Japan), and then applied to a Sephacryl S-300 HR (GE Healthcare Bioscience, U.S.A.) column (diameter: 25 cm, height: 85 cm) equilibrated with a 20 mM phosphate buffer (pH 7.3) containing 50 mM sodium chloride. An elution peak with the maximum absorbance at 280 nm was separated, and concentrated to about 0.8 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 1 L/hour.

The purified solution 3 was passed through a virus-removing membrane, PLANOVA 15N (membrane area: 0.3 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a purified product of soluble thrombomodulin (lot: B1).

The APC activity of thrombomodulin of B1 was 79000 U/mL.

Soluble thrombomodulin concentration in the solution of B1 was 12.6 mg/mL.

Comparative Example 3

Preparation of Soluble Thrombomodulin 3

The DMEM medium (Invitrogen, U.S.A.) was used as the base medium. Growth medium was obtained by adding 150 mg/L of L-proline (Ajinomoto, Japan), 60 mg/L of kanamycin sulfate (MeijiSeika Pharma, Japan), 1 mg/L of tylosin tartrate (Mercian, Japan), and 10% bovine serum (HyClone, U.S.A.) to the base medium, and used. Further, production medium was the same as the growth medium, provided that the serum concentration was changed to 1 to 3%.

The cells of one vial prepared in Comparative Example 1 were thawed, inoculated into 100 mL of the growth medium, and cultured with stirring at 37° C. for 5 days by using a spinner flask in a $CO_2$ incubator. The entire volume of the culture medium was transferred to 400 mL of the growth medium, and the cells were cultured with stirring at 37° C. for 5 days by using a spinner flask in a $CO_2$ incubator. The entire volume of the culture medium was transferred to 1.6 L of the growth medium, and the cells were cultured with stirring at 37° C. for 5 days by using a spherical bottle with bubbling air and $CO_2$ into the medium. The entire volume of the culture medium was transferred to 6 L of the growth medium, and the cells were cultured with stirring at 37° C. for 5 days by using a spherical bottle with bubbling air and $CO_2$ into the medium. The entire volume of the culture medium was transferred to 56 L of the growth medium, and the cells were cultured with stirring at 37° C. for 4 days by using a spherical bottle with bubbling air and $CO_2$ into the medium. After the entire medium was exchanged, the cells were further cultured for 3 days. Further, after the entire medium was exchanged, and when the living cell density reached $1.0 \times 10^6$ cells/mL, the medium was changed to the production medium. The production solution was collected every day by using a continuous centrifugation machine CC-100 (Alfa Laval, Sweden), and the fresh medium was supplemented. The production culture was carried out for 100 days. The collected production solution was clarified by using filtration filters having pore diameters of 0.7 μm and 0.22 μm (Pall, U.S.A.), and stored at 2 to 10° C. as a filtered production solution.

About 2400 L of the filtered production solution was applied to a Q-Sepharose Fast Flow (GE Healthcare, U.S.A.) column (diameter: 44 cm, height: 25 cm) equilibrated with a 20 mM Tris-hydrochloric acid buffer (pH 7.4) containing 150 mM sodium chloride. Then, the column was washed with 6 CV of a 20 mM acetate buffer (pH 5.5) containing 180 mM sodium chloride, and further washed with 2 CV of a 20 mM Tris-hydrochloric acid buffer (pH 7.4) containing 180 mM sodium chloride. Elution was started with a 20 mM Tris-hydrochloric acid buffer (pH 7.4) containing 300 mM sodium chloride, and about 15 L of the eluate from the start of the peak of absorbance at 280 nm was obtained as a roughly purified solution. The operation was performed at a temperature of 2 to 10° C., and a chromatography flow rate of 45 L/hour.

The aforementioned roughly purified solution 1 was applied to a Butyl-Sepharose FF (GE Healthcare Bioscience, U.S.A.) column (diameter: 25 cm. height: 10 cm) equilibrated with a 20 mM phosphate buffer (pH 7.0) containing 0.3 M NaCl. Washing was started with a 20 mM phosphate buffer (pH 7.0) containing 0.3 M NaCl, and a flow-through fraction corresponding to the start to the end of the peak of absorbance at 280 nm was obtained as a roughly purified solution 2. The operation was performed at a temperature of 2 to 10° C., and a chromatography flow rate of 13 L/hour.

About 20 L of the roughly purified solution was applied to a monoclonal antibody column (diameter: 44 cm, height: 18 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 1 M glycine-sodium hydroxide buffer (pH 9.0) and 1/25 volume of a 0.5 M phosphate buffer (pH 7.3) to obtain a purified solution 1. The operation was performed at a temperature of 2 to 10° C., and a chromatography flow rate of 50 L/hour.

About 15 L of the purified solution 1 was concentrated to about 1 L by using an ultrafiltration membrane, Microza UF Module SIP-1013 (Asahi Kasei Chemicals, Japan), and then applied to a Sephacryl S-300 HR (GE Healthcare Bioscience, U.S.A.) column (diameter: 25 cm, height: 80 cm) equilibrated with a 20 mM phosphate buffer (pH 7.3) containing 150 mM sodium chloride. The operation was performed at a temperature of 2 to 10° C., and a chromatography flow rate of 1 L/hour. An elution peak with the maximum absorbance at 280 nm was separated, and passed through a 0.22-μm PVDF filtration membrane (Millipore, U.S.A.) to collect about 3 L of the eluate. The result was used as a purified product of soluble thrombomodulin (lot: B2).

The APC activity of thrombomodulin of B2 was 28000 U/mL.

Soluble thrombomodulin concentration in the solution of B2 was 3.8 mg/mL.

Comparative Example 4

Preparation of Soluble Thrombomodulin 4

The cells of one vial cryopreserved in Comparative Example 1 were thawed, inoculated into a serum-free medium IS CHO-CD (Irvine Scientific, U.S.A.) containing 8 mM L-glutamine (Invitrogen, U.S.A.), 50 μM hypoxanthine (Invitrogen, U.S.A.), and 8 μM thymidine (Invitrogen, U.S.A.), and cultured at 37° C. in a $CO_2$ incubator. The cells obtained by centrifuging the culture medium was suspended in the serum-free medium IS CHO-CD (Irvine Scientific, U.S.A.) containing 8 mM L-glutamine (Invitrogen, U.S.A.), 50 μM hypoxanthine (Invitrogen, U.S.A.), 8 μM thymidine (Invitrogen, U.S.A.), and 10% dimethyl sulfoxide (Sigma-Aldrich, U.S.A.), and then the medium was dispensed into vials ($2 \times 10^7$ cells/vial), and cryopreserved in liquid nitrogen.

Growth medium was prepared by dissolving 20.78 g of IS CHO-CD-A3 (Irvine Scientific, U.S.A.), 4.06 g of sodium chloride (Tomita Pharmaceutical, Japan), and 2.20 g of sodium hydrogencarbonate (Wako Pure Chemical Industries, Japan) in 1 L of water. Production medium was prepared by dissolving 20.78 g of IS CHO-CD-A3 (Irvine Scientific, U.S.A.), 2.63 g of sodium chloride (Tomita Pharmaceutical, Japan), and 4.40 g of sodium hydrogencarbonate (Wako Pure Chemical Industries, Japan) in 1 L of water.

The cells of one vial were thawed, inoculated into 100 mL of the growth medium, and cultured at 36° C. for 5 days as stationary culture by using a T-flask in a $CO_2$ incubator. When the living cell density became $7.0 \times 10^5$ cells/mL or more, 40 mL of the culture medium was transferred to 360 mL of the growth medium, and the cells were cultured with stirring at 36° C. for 7 days by using a spinner flask in a $CO_2$ incubator. When the living cell density became $7.0 \times 10^5$ cells/mL or more, 80 mL of the culture medium was transferred to 720 mL of the growth medium, and the cells were cultured with stirring at 36° C. for 6 days by using a spinner flask in a $CO_2$ incubator. When the living cell density became $7.0 \times 10^5$ cells/mL or more, the entire volume of the culture medium was transferred to 9.2 L of the growth medium, and the cells were cultured with stirring at 36° C., pH 7.1 and 50% of dissolved oxygen for 8 days by using a perfusion culture tank. When the living cell density became $7.0 \times 10^5$ cells/mL or more, perfusion culture was started, in which the production medium was continuously added, and the culture supernatant was continuously collected. The culture conditions consisted of 36° C., pH 7.1, dissolved oxygen: 50%, medium exchange: 10 L/day, and surface pressurization: 0 to 0.2 MPa. After the living cell density reached $7.5 \times 10^6$ cells/mL, the culture was further continued for 26 days, and the culture supernatant was collected as a production solution.

The collected production solution was clarified by using filtration filters, SUPRAcap (Pall, U.S.A.) and Supor EBV (Pall, U.S.A.), and stored at 2 to 10° C. as a filtered production solution.

About 250 L of the filtered production solution was applied to a Q-Sepharose Fast Flow (GE Healthcare, U.S.A.) column (diameter: 25 cm, height: 25 cm) equilibrated with a 20 mM Tris-hydrochloric acid buffer (pH 7.7) containing 150 mM sodium chloride. Then, the column was washed with 6 CV of a 20 mM acetate buffer (pH 5.6) containing 180 mM sodium chloride, and further washed with 4 CV of a 20 mM Tris-hydrochloric acid buffer (pH 7.7) containing 180 mM sodium chloride. Elution was started with a 20 mM Tris-hydrochloric acid buffer (pH 7.7) containing 290 mM sodium chloride, and 0.5 column volume of the eluate from the start of the peak of absorbance at 280 nm was obtained as a roughly purified solution. The operation was performed at a temperature of 2 to 10° C., and a chromatography flow rate of 18 L/hour.

About 6 L of the roughly purified solution was applied to a monoclonal antibody column (diameter: 44 cm, height: 8 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The operation was performed at a temperature of 2 to 10° C., and a chromatography flow rate of 46 L/hour.

About 14 L of the purified solution 1 was adjusted to pH 3.5 with a 1.0 M glycine-hydrochloric acid buffer (pH 2.0), and applied to an SP-Sepharose FF (GE Healthcare Bioscience, U.S.A.) column (diameter: 14 cm, height: 13 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 15 L/hour.

About 20 L of the purified solution 2 was concentrated to about 1 L by using an ultrafiltration membrane, Microza UF Module SIP-1013 (Asahi Kasei Chemicals, Japan), and then applied to a Sephacryl S-300 HR (GE Healthcare Bioscience, U.S.A.) column (diameter: 25 cm, height: 79 cm) equilibrated with a 20 mM phosphate buffer (pH 7.3) containing 50 mM sodium chloride. An elution peak with the maximum absorbance at 280 nm was separated, and concentrated to about 0.7 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 1 L/hour.

The entire volume of the purified solution 3 was passed through a virus-removing membrane, PLANOVA 15N (membrane area: 0.12 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a purified product of soluble thrombomodulin (lot: B3).

Example 1

Preparation of Highly-purified Soluble Thrombomodulin 1

Cell culture was performed by using, as the base medium, the medium described in Japanese Patent Unexamined Publication No. 11-341990, Ingredient Table 2, provided that $NaHCO_3$ concentration was changed to 5,700 mg/L, and NaCl concentration was changed to 2,410 mg/L. Growth medium was obtained by adding 60 mg/L of kanamycin sulfate (Invitrogen, U.S.A.), 1 mg/L of tylosin tartrate (Sigma-Aldrich, U.S.A.), and 8% bovine serum (HyClone, U.S.A.) to the base medium, and used. Further, production medium was the same as the growth medium, provided that the serum concentration was changed to 3%.

The cells of one vial prepared in Comparative Example 1 were thawed, inoculated into 100 mL of the growth medium, and cultured with stirring at 37° C. for 5 days by using a spinner flask in a $CO_2$ incubator. When the living cell density became $7.0 \times 10^5$ cells/mL or more, the entire volume of the culture medium was transferred to 0.9 L of the growth medium, and the cells were cultured with stirring at 37° C. for 5 days by using a spinner flask in a $CO_2$ incubator. When the living cell density became $7.0 \times 10^5$ cells/mL or more, the entire volume of the culture medium was transferred to 9 L of the growth medium, and the cells were cultured with stirring at 37° C., pH 7.2 and 50% of dissolved oxygen for 5 days by using a culture tank. When the living cell density became $7.0 \times 10^5$ cells/mL or more, the entire volume of the culture medium was transferred to 120 L of the growth medium, and the cells were cultured with stirring at 37° C., pH 7.2 and 50% of dissolved oxygen for 7 days by using a perfusion culture tank. When the living cell density became $7.0 \times 10^5$ cells/mL or more, perfusion culture was started, in which the production medium was continuously added, and the culture supernatant was continuously collected. The culture conditions consisted of 37° C., pH 7.2, dissolved oxygen: 50%, medium exchange: 130 to 200 L/day, and surface pressurization: 0 to 0.2 MPa. After the living cell density reached $7.5 \times 10^6$ cells/mL, the culture was further continued for 40 days, and the culture supernatant was collected as a production solution. The collected production solution was clarified by using filtration filters, SUPRAdisc (Pall, U.S.A.) and Supor EBV (Pall, U.S.A.), and stored at 2 to 10° C. as a filtered production solution.

About 700 L of the filtered production solution was applied to a Q-Sepharose Fast Flow (GE Healthcare, U.S.A.) column (diameter: 63 cm, height: 25 cm) equilibrated with a 20 mM Tris-hydrochloric acid buffer (pH 7.7) containing 150 mM sodium chloride. Then, the column was washed with 6 CV of a 20 mM acetate buffer (pH 5.5) containing 180 mM sodium chloride, and further washed with a 20 mM Tris-hydrochloric acid buffer (pH 7.7) containing 180 mM sodium chloride until absorbance at 280 nm returned to the baseline. Elution was started with a 20 mM Tris-hydrochloric acid buffer (pH 7.7) containing 300 mM sodium chloride, and 0.5 column volume of the eluate from the start of the peak of absorbance at 280 nm was obtained as a roughly purified solution. The same operation was repeated 3 times to obtain 3 lots of the roughly purified solution. The operation was performed at a temperature of 2 to 10° C., and a chromatography flow rate of 109 L/hour.

About 20 L of the roughly purified solution was applied to a monoclonal antibody column (diameter: 44 cm, height: 13 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The same operation was repeated 6 times to obtain 6 lots of the purified solution 1. The operation was performed at a temperature of 2 to 10° C., and a chromatography flow rate of 46 L/hour.

About 130 L of the purified solution 1 of the 6 lots was passed through a nylon filtration membrane (pore diameter: 0.4 μm+0.2 μm, membrane area: 1.8 $m^2$, SARTOLON Maxi Caps 5101307H3, Sartorius, Germany) at a flow rate of 5 L/minute (about 0.07 $m^2$ of membrane area was used for 1 mg of HCP), adjusted to pH 3.5 with a 1.0 M glycine-hydrochloric acid buffer (pH 2.0), and applied to an SP-Sepharose FF (GE Healthcare Bioscience, U.S.A.) column (diameter: 45 cm, height: 10 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 160 L/hour.

About 160 L of the purified solution 2 was concentrated to about 10 L by using an ultrafiltration membrane, Microza UF Module SIP-2013 (Asahi Kasei Chemicals, Japan), and then applied to a Sephacryl S-300 HR (GE Healthcare Bioscience, U.S.A.) column (diameter: 63 cm, height: 94 cm) equilibrated with a 20 mM phosphate buffer (pH 7.3) containing 50 mM sodium chloride. An elution peak with the maximum absorbance at 280 nm was separated, and concentrated to about 6 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 6.2 L/hour.

The purified solution 3 was passed through a virus-removing membrane, PLANOVA 15N (membrane area: 1 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a highly-purified soluble thrombomodulin purified product (lot: A4).

The APC activity of thrombomodulin of A4 was 60000 U/mL.

Soluble thrombomodulin concentration in the solution of A4 was 9.3 mg/mL.

Example 2

Preparation of Highly-purified Soluble Thrombomodulin 2

About 2,000 L of the filtered production solution obtained in Example 1 was applied to a Q-Sepharose Fast Flow (GE Healthcare, U.S.A.) column (diameter: 63 cm, height: 25 cm) equilibrated with a 20 mM Tris-hydrochloric acid buffer (pH 7.7) containing 150 mM sodium chloride. Then, the column was washed with 6 CV of a 20 mM acetate buffer (pH 5.45) containing 170 mM sodium chloride, and further washed with 4 CV of a 20 mM Tris-hydrochloric acid buffer (pH 7.7) containing 170 mM sodium chloride. Elution was started with a 20 mM Tris-hydrochloric acid buffer (pH 7.7) containing 300 mM sodium chloride, and 0.5 column volume of the eluate from the start of the peak of absorbance at 280 nm was obtained as a roughly purified solution. The same operation was repeated twice to obtain 2 lots of the roughly purified solution. The operation was performed at a temperature of 2 to 10° C., and a chromatography flow rate of 109 L/hour.

About 10 L of the roughly purified solution was applied to a monoclonal antibody column (diameter: 44 cm, height: 13 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The same operation was repeated 8 times to obtain 8 lots of the purified solution 1. The operation was performed at a temperature of 2 to 10° C., and a chromatography flow rate of 46 L/hour.

About 180 L of the purified solution 1 for 6 lots was passed through a nylon filtration membrane (pore diameter: 0.4 μm+0.2 μm, membrane area: 1.8 $m^2$, SARTOLON Maxi Caps 5101307H3, Sartorius, Germany) at a flow rate of 5 L/minute (about 0.05 $m^2$ of membrane area was used for 1 mg of HCP), adjusted to pH 3.5 with a 1.0 M glycine-hydrochloric acid buffer (pH 2.0), and applied to an SP-Sepharose FF (GE Healthcare Bioscience, U.S.A.) column (diameter: 45 cm, height: 10 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 160 L/hour.

About 220 L of the purified solution 2 was concentrated to about 5 L by using an ultrafiltration membrane, Microza UF Module SIP-2013 (Asahi Kasei Chemicals, Japan), and then applied to a Sephacryl S-300 HR (GE Healthcare Bioscience, U.S.A.) column (diameter: 63 cm, height: 94 cm) equilibrated with a 20 mM phosphate buffer (pH 7.3) containing 50 mM sodium chloride. An elution peak with the maximum absorbance at 280 nm was separated, and concentrated to about 10 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 6.2 L/hour.

The purified solution 3 was passed through a virus-removing membrane, PLANOVA 15N (membrane area: 1 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a highly-purified soluble thrombomodulin purified product (lot: A5).

The APC activity of thrombomodulin of A5 was 69000 U/mL.

Soluble thrombomodulin concentration in the solution of A5 was 10.9 mg/mL.

Example 3

Preparation of Highly-purified Soluble Thrombomodulin 3

Cell culture was performed by using, as the base medium, the medium described in Japanese Patent Unexamined Publication No. 11-341990, Ingredient Table 2, provided that NaHCO$_3$ concentration was changed to 5,700 mg/L, and NaCl concentration was changed to 2,410 mg/L. Growth medium was obtained by adding 60 mg/L of kanamycin sulfate (Invitrogen, U.S.A.), 1 mg/L of tylosin tartrate (Sigma-Aldrich, U.S.A.), and 8% bovine serum (HyClone, U.S.A.) to the base medium, and used. Further, production medium was the same as the growth medium, provided that the serum concentration was changed to 3%.

The cells of one vial prepared in Comparative Example 1 were thawed, inoculated into 100 mL of the growth medium, and cultured with stirring at 37° C. for 5 days by using a spinner flask in a CO$_2$ incubator. When the living cell density became 7.0×10$^5$ cells/mL or more, the entire volume of the culture medium was transferred to 0.9 L of the growth medium, and the cells were cultured with stirring at 37° C. for 5 days by using a spinner flask in a $CO_2$ incubator. When the living cell density became $7.0\times10^5$ cells/mL or more, the entire volume of the culture medium was transferred to 9 L of the growth medium, and the cells were cultured with stirring at 37° C., pH 7.2 and 50% of dissolved oxygen for 5 days by using a culture tank. When the living cell density became $7.0\times10^5$ cells/mL or more, the entire volume of the culture medium was transferred to 120 L of the growth medium, and the cells were cultured with stirring at 37° C., pH 7.2 and 50% of dissolved oxygen for 7 days by using a perfusion culture tank. When the living cell density became $7.0\times10^5$ cells/mL or more, perfusion culture was started, in which the production medium was continuously added, and the culture supernatant was continuously collected. The culture conditions consisted of 37° C., pH 7.2, dissolved oxygen: 50%, medium exchange: 130 to 200 L/day, and surface pressurization: 0 to 0.2 MPa. After the living cell density reached $7.5\times10^6$ cells/mL, the culture was further continued for 36 days, and the culture supernatant was collected as a production solution. The collected production solution was clarified by using filtration filters, SUPRAdisc II (Pall, U.S.A.) and Supor EBV (Pall, U.S.A.), and stored at 2 to 10° C. as a filtered production solution.

About 700 L of the filtered production solution was applied to a Q-Sepharose Fast Flow (GE Healthcare, U.S.A.) column (diameter: 63 cm, height: 25 cm) equilibrated with a 20 mM Tris-hydrochloric acid buffer (pH 7.7) containing 150 mM sodium chloride. Then, the column was washed with 6 CV of a 20 mM acetate buffer (pH 5.5) containing 180 mM sodium chloride, and further washed with a 20 mM Tris-hydrochloric acid buffer (pH 7.7) containing 180 mM sodium chloride until absorbance at 280 nm returned to the baseline. Elution was started with a 20 mM Tris-hydrochloric acid buffer (pH 7.7) containing 300 mM sodium chloride, and 0.5 column volume of the eluate from the start of the peak of absorbance at 280 nm was obtained as a roughly purified solution. The same operation was repeated 6 times to obtain 6 lots of the roughly purified solution. The operation was performed at a temperature of 2 to 10° C., and a chromatography flow rate of 109 L/hour.

About 20 L of the roughly purified solution was applied to a monoclonal antibody column (diameter: 44 cm, height: 13 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with 1/10 volume of a 0.5 M phosphate buffer (pH 7.3) to obtain a purified solution 1. The same operation was repeated 12 times to obtain 12 lots of the purified solution 1. The operation was performed at a temperature of 2 to 10° C., and a chromatography flow rate of 46 L/hour.

About 270 L of the purified solution 1 of the 12 lots was passed through a nylon filtration membrane (pore diameter: 0.4 μm+0.2 μm, membrane area: 1.8 $m^2$, SARTOLON Maxi Caps 5101307H3, Sartorius, Germany) at a flow rate of 5 L/minute (about 0.05 $m^2$ of membrane area was used for 1 mg of HCP), adjusted to pH 3.5 with a 1.0 M glycine-hydrochloric acid buffer (pH 2.0), and applied to an SP-Sepharose FF (GE Healthcare Bioscience, U.S.A.) column (diameter: 45 cm, height: 10 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 160 L/hour.

About 300 L of the purified solution 2 was concentrated to about 11 L by using an ultrafiltration membrane, Microza UF Module SIP-2013 (Asahi Kasei Chemicals, Japan), and then applied to a Sephacryl S-300 HR (GE Healthcare Bioscience, U.S.A.) column (diameter: 63 cm, height: 94 cm) equilibrated with a 20 mM phosphate buffer (pH 7.3) containing 50 mM sodium chloride. An elution peak with the maximum absorbance at 280 nm was separated, and concentrated to about 13 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 6.2 L/hour.

The purified solution 3 was passed through a virus-removing membrane, PLANOVA 15N (membrane area: 1 $m^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a highly-purified soluble thrombomodulin purified product (lot: A6).

The APC activity of thrombomodulin of A6 was 81000 U/mL.

Soluble thrombomodulin concentration in the solution of A6 was 11.9 mg/mL.

Example 4

Preparation of Highly-purified Soluble Thrombomodulin 4

Growth medium was prepared by dissolving 20.78 g of IS CHO-CD-A3 (Irvine Scientific, U.S.A.), 4.06 g of sodium chloride (Tomita Pharmaceutical, Japan), and 2.20 g of sodium hydrogencarbonate (Wako Pure Chemical Industries, Japan) in 1 L of water. Production medium was prepared by dissolving 20.78 g of IS CHO-CD-A3 (Irvine Scientific, U.S.A.), 2.63 g of sodium chloride (Tomita Pharmaceutical, Japan), and 4.40 g of sodium hydrogencarbonate (Wako Pure Chemical Industries, Japan) in 1 L of water.

The cells of one vial prepared in Comparative Example 4 were thawed, inoculated into 100 mL of the growth medium, and cultured at 36° C. for 5 days as stationary culture by using a T-flask in a $CO_2$ incubator. When the living cell density became $7.0\times10^5$ cells/mL or more, the entire volume of the culture medium was transferred to 0.9 L of the growth medium, and the cells were cultured with stirring at 36° C. for 5 days by using a spinner flask in a $CO_2$ incubator. When the living cell density became $7.0\times10^5$ cells/mL or more, the entire volume of the culture medium was transferred to 9 L of the growth medium, and the cells were cultured with stirring at 36° C., pH 7.1 and 50% of dissolved oxygen for 5 days by using a culture tank. When the living cell density became $7.0\times10^5$ cells/mL or more, the entire volume of the culture medium was transferred to 120 L of the growth medium, and the cells were cultured with stirring at 36° C., pH 7.1 and 50% of dissolved oxygen for 7 days by using a perfusion culture tank. When the living cell density became $7.0\times10^5$ cells/mL or more, perfusion culture was started, in which the production medium was continuously added, and the culture supernatant was continuously collected. The culture conditions consisted of 36° C., pH 7.1, dissolved oxygen: 50%, medium exchange: 130 L/day, and surface pressurization: 0 to 0.2 MPa. After the living cell density reached 7.5×10$^6$ cells/mL, the culture was further continued for 20 days, and the culture supernatant was collected as a production solution.

The collected production solution was clarified by using filtration filters, SUPRAdisc II (Pall, U.S.A.) and Supor EBV (Pall, U.S.A.), and stored at 2 to 10° C. as a filtered production solution.

About 1,400 L of the filtered production solution was applied to a Q-Sepharose Fast Flow (GE Healthcare, U.S.A.) column (diameter: 63 cm, height: 25 cm) equilibrated with a 20 mM Tris-hydrochloric acid buffer (pH 7.7) containing 150 mM sodium chloride. Then, the column was washed with 6 CV of a 20 mM acetate buffer (pH 5.6) containing 180 mM sodium chloride, and further washed with 4 CV of a 20 mM Tris-hydrochloric acid buffer (pH 7.7) containing 180 mM sodium chloride. Elution was started with a 20 mM Tris-hydrochloric acid buffer (pH 7.7) containing 290 mM sodium chloride, and 0.5 column volume of the eluate from the start of the peak of absorbance at 280 nm was obtained as a roughly purified solution. The same operation was performed also for about 900 L of the filtered production solution, and thus 2 lots of the roughly purified solution were obtained. The operation was performed at a temperature of 2 to 10° C., and a chromatography flow rate of 109 L/hour.

About 13 L of the roughly purified solution was applied to a monoclonal antibody column (diameter: 44 cm, height: 13 cm) equilibrated with a 20 mM phosphate buffer (pH 7.3) containing 0.3 M sodium chloride. 6 CV of a 20 mM phosphate buffer (pH 7.3) containing 1.0 M sodium chloride was poured into the column, 3 CV of a 0.1 M acetate buffer (pH 5.0) was further poured to wash the column, and elution was started with a 0.1 M glycine-hydrochloric acid buffer (pH 3.0) containing 0.3 M sodium chloride. The eluate corresponding to the start to the end of the peak of absorbance at 280 nm was obtained, and added with ⅒ volume of a 0.5 M phosphate buffer (pH 7.3) to obtain a purified solution 1. The same operation was repeated 5 times to obtain 5 lots of the purified solution 1. The operation was performed at a temperature of 2 to 10° C., and a chromatography flow rate of 46 L/hour.

About 110 L of the purified solution 1 of the 5 lots was passed through a nylon filtration membrane (pore diameter: 0.4 μm+0.2 μm, membrane area: 1.8 m$^2$, SARTOLON Maxi Caps 5101307H3, Sartorius, Germany) at a flow rate of 5 L/minute (about 0.03 m$^2$ of membrane area was used for 1 mg of HCP), adjusted to pH 3.5 with a 1.0 M glycine-hydrochloric acid buffer (pH 2.0), and applied to an SP-Sepharose FF (GE Healthcare Bioscience, U.S.A.) column (diameter: 45 cm, height: 10 cm) equilibrated with a 0.1 M glycine-hydrochloric acid buffer (pH 3.5) containing 0.3 M NaCl. Washing was started with a 0.1 M glycine-hydrochloric acid buffer (pH 3.5) containing 0.3 M NaCl, and a flow-through fraction corresponding to the start to the end of the peak of absorbance at 280 nm was obtained, and immediately neutralized to pH 7 with a 0.5 M phosphate buffer (pH 7.3) to obtain a purified solution 2. The operation was performed at a temperature of 2 to 10° C., and a chromatography flow rate of 160 L/hour.

About 120 L of the purified solution 2 was concentrated to about 5 L by using an ultrafiltration membrane, Microza UF Module SIP-2013 (Asahi Kasei Chemicals, Japan), and then applied to a Sephacryl S-300 HR (GE Healthcare Bioscience, U.S.A.) column (diameter: 63 cm, height: 94 cm) equilibrated with a 20 mM phosphate buffer (pH 7.3) containing 50 mM sodium chloride. An elution peak with the maximum absorbance at 280 nm was separated, and concentrated to about 5 L by using an ultrafiltration membrane, Microza UF Module SIP-1013 (Asahi Kasei Chemicals, Japan), to obtain a purified solution 3. The operation was performed at a temperature of 2 to 10° C., and a chromatography flow rate of 6.2 L/hour.

The entire volume of the purified solution 3 was passed through a virus-removing membrane, PLANOVA 15N (membrane area: 1 m$^2$, Asahi Kasei Medical, Japan), equilibrated with a 20 mM phosphate buffer (pH 7.3) containing 50 mM sodium chloride at room temperature and a pressure lower than 0.1 MPa, and then further passed through a 0.22-μm PVDF filtration membrane (Millipore, U.S.A.), and the entire volume of the solution was collected. The result was used as a highly-purified soluble thrombomodulin purified product (lot: A7).

The APC activity of thrombomodulin of A7 was 69000 U/mL.

Soluble thrombomodulin concentration in the solution of A7 was 10.4 mg/mL.

Test Example 1

Evaluation of Removal of HCP Using Various Filtration Membranes

The purified solution 1 obtained in Comparative Example 1 (HCP concentration: 462 ng/ml) was passed through filtration membranes of different materials, and HCP concentrations of the filtrates were compared. Specifically, 5 ml of the purified solution 1 was passed at a flow rate of 1 ml/minute through each of filtration membranes made of (1) PVDF (polyvinylidene fluoride) (Millex GV, Millipore, U.S.A.), (2) CA (cellulose acetate) (Minisart, Sartorius, Germany), (3) PES (polyethersulfone) (Minisart High-Flow, Sartorius, Germany), (4) nylon (NALGENE Syringe Filter, Thermo Fisher Scientific, U.S.A.), and (5) CA+GF (cellulose acetate+glass fiber) (Minisart Plus, Sartorius), and the entire volume was collected as a filtrate.

Protein concentration and HCP concentration of the solution were measured before and after the filtration. The protein concentration was obtained on the basis of absorbance at 280 nm, and the HCP concentration was measured according to the method described in Reference Example 2. As a result, substantial difference was not observed between the protein concentrations measured before and after the filtration for all the filtration membranes, but high HCP-removing effect was observed for the filtration membrane made of nylon and the filtration membrane made of PES, and it was found that they reduced the HCP concentration to 28% and 36%, respectively (Table 1). Further, degree of the reduction of the HCP concentration significantly differed depending on the material of the membrane in spite of the same pore diameter. Accordingly, it was not considered that HCP insolubilized by aggregation was removed, but it was considered that HCP was removed by adsorption by the membranes. The diameters of the evaluated filtration membranes were 25 mm or 26 mm, and the membrane areas for 1 mg of HCP calculated on the basis of effective membrane areas of the filtration membranes described in the data sheets of the manufacturers were 0.17 m$^2$ or 0.23 m$^2$.

TABLE 1

| Filtration membrane | Pore diameter (μm) | Membrane diameter (mm) | Effective membrane area (cm$^2$) | Membrane area for 1 mg of HCP (m$^2$) | Recovery of HCP (%) | Recovery of proteins (%) |
|---|---|---|---|---|---|---|
| (1) PVDF | 0.22 | 25 | 3.9 | 0.17 | 93 | 101 |
| (2) CA | 0.2 | 26 | 5.3 | 0.23 | 69 | 100 |
| (3) PES | 0.2 | 26 | 5.3 | 0.23 | 36 | 100 |
| (4) Nylon | 0.2 | 25 | Unknown | Unknown | 28 | 99 |
| (5) CA + GF | 0.2 | 26 | 5.3 | 0.23 | 44 | 99 |

Test Example 2

Comparison of HCP-removing Abilities of Nylon and PES Filtration Membranes

It was found in Test Example 1 that the nylon filtration membrane and the PES filtration membrane had high HCP-removing abilities. Accordingly, change of HCP-removing abilities of these filtration membranes depending on the volume of solution passed through them was evaluated. Products of two manufacturers were prepared for each material of the filtration membrane, and the purified solution 1 of a lot different from the lots used in Test Example 1 was passed through the membranes (HCP concentration: 303 ng/ml). The filtration membranes used were a PVDF filtration membrane (pore diameter: 0.22 μm, membrane diameter: 25 mm, effective membrane area: 3.9 cm$^2$, Millex GV, Millipore, U.S.A.) as a control, (1) Acrodisc AP-4436T, Pall, U.S.A., pore diameter: 0.2 μm, membrane diameter: 25 mm, effective membrane area: 3.9 cm$^2$, and (2) Minisart NY25, Sartorius, Germany, pore diameter: 0.2 μm, membrane diameter 25 mm, effective membrane area: 4.8 cm$^2$ as nylon filtration membranes, as well as (3) Acrodisc PN4612, Pall, U.S.A., pore diameter: 0.2 μm, membrane diameter 25 mm, effective membrane area: 2.8 cm$^2$, and (4) Minisart High-Flow, Sartorius, Germany, pore diameter: 0.2 μm, membrane diameter 26 mm, effective membrane area: 5.3 cm$^2$ as PES filtration membranes. The purified solution 1 was passed through each filtration membrane in a volume of 100 ml at a flow rate of 10 ml/minute, and the filtrate was sampled for every 20 ml of the solution passed through the filtration membrane, of which HCP concentration was measured according to the method described in Reference Example 2, and of which protein concentration was obtained on the basis of absorbance at 280 nm.

As a result, change of the protein concentration was not observed for all the samples, but HCP-removing effect was observed for both the nylon and PES filtration membranes (Table 2). The nylon filtration membrane gave especially high HCP-removing effect, and reduced the HCP concentration to 25% at most. It was found that when volume of the solution passed through the filtration membrane was smaller, i.e., filtration membrane area for 1 mg of HCP was larger, higher HCP-removing effect was obtained.

TABLE 2

| Filtration membrane | | Membrane area for 1 mg of HCP (m$^2$) | Recovery of HCP (%) | | | | |
|---|---|---|---|---|---|---|---|
| | | | 20 ml | 40 ml | 60 ml | 80 ml | 100 ml |
| PVDF | | 0.013~0.064 | 94 | 98 | 109 | 89 | 92 |
| Nylon | (1) Pall | 0.013~0.064 | 50 | 62 | 60 | 69 | 75 |
| | (2) Sartorius | 0.016~0.079 | 25 | 34 | 30 | 49 | 47 |
| PES | (3) Pall | 0.009~0.046 | 77 | 84 | 98 | 88 | 107 |
| | (4) Sartorius | 0.017~0.087 | 68 | 66 | 75 | 62 | 63 |

Test Example 3

Evaluation of HCP-removing Ability of Nylon Filtration Membrane for Different Solution Compositions Effects of differences in buffer composition and soluble thrombomodulin concentration on the HCP-removing ability of a nylon filtration membrane were evaluated. Each of the purified solution 1, the purified solution 2, the purified solution 2 after the concentration, the purified solution 3, and the purified product obtained in Comparative Example 4 in a volume of 5 mL was passed through a nylon filtration membrane having a membrane diameter of 25 mm, an effective membrane area of 4.8 cm$^2$, and a pore diameter of 0.2 μm (Minisart NY25, Sartorius, Germany) at a flow rate of 1 mL/minute, and the entire volume was collected as a filtrate. The filtration membrane areas for 1 mg of HCP contained in the samples were as follows: 0.77 m$^2$ for the purified solution 1, 1.7 m$^2$ for the purified solution 2, 0.43 m$^2$ for the purified solution 2 after the concentration, 0.72 m$^2$ for the purified solution 3, and 0.81 m$^2$ for the purified product. HCP concentration of each obtained filtrate was measured according to the method described in Reference Example 2, and protein concentration of the same was obtained on the basis of absorbance at 280 nm. As a result, the nylon membrane gave high HCP-removing effect for all the samples, and provided high protein recovery higher than 90% (Table 3).

TABLE 3

| | HCP | | | Protein | | |
|---|---|---|---|---|---|---|
| Sample | Before filtration (ng/mL) | After filtration (ng/mL) | Recovery (%) | Before filtration (mg/mL) | After filtration (mg/mL) | Recovery (%) |
| Purified solution 1 | 125 | 65 | 52 | 0.47 | 0.44 | 94 |
| Purified solution 2 | 56 | 35 | 63 | 0.40 | 0.37 | 93 |

TABLE 3-continued

| Sample | HCP | | | Protein | | |
|---|---|---|---|---|---|---|
| | Before filtration (ng/mL) | After filtration (ng/mL) | Recovery (%) | Before filtration (mg/mL) | After filtration (mg/mL) | Recovery (%) |
| Purified solution 2 after concentration | 222 | 115 | 52 | 8.28 | 8.28 | 100 |
| Purified solution 3 | 134 | <25 | <19 | 11.1 | 11.4 | 103 |
| Purified product | 119 | <25 | <21 | 10.1 | 10.3 | 102 |

Test Example 4

Evaluation of Removal of HCP from Purified Products of Soluble Thrombomodulin Obtained by Various Preparation Methods It was examined whether or not HCP was successfully removed from soluble thrombomodulin products obtained by different methods by further passing them through a nylon filtration membrane. The soluble thrombomodulin purified products obtained in Comparative Examples 1 to 3 (A1, B1 and B2, respectively) in a volume of 5 mL each were passed through a nylon filtration membrane having a membrane diameter 25 mm, an effective membrane area: 4.8 cm$^2$, and a pore diameter: 0.2 μm (Minisart NY25, Sartorius, Germany) at a flow rate of 1 mL/minute, and the entire volume of each was collected as a filtrate. The filtration membrane areas for 1 mg of HCP contained in the soluble thrombomodulin purified products were 0.34 m$^2$ for A1, 0.46 m$^2$ for B1, and 1.7 m$^2$ for B2. HCP contents, mouse IgG contents, and bovine serum protein contents of the solutions were measured before and after the filtration by the methods described in Reference Examples 2 to 4. The nylon membrane gave high removing effect for only HCP for all the purified products (Table 4). On the basis of this result, it was considered that the nylon filtration membrane did not have an action of non-specifically adsorbing proteins, but had an action of specifically adsorbing HCP.

trial level production using a nylon filtration membrane (Examples 1 to 4) were measured by the methods described in Reference Examples 2 to 4.

The three lots of Comparative Example 1 (A1, A2 and A3) not passed through any nylon filtration membrane had high HCP contents higher than 10 ng/10,000 U, whilst the HCP contents of the four lots of Examples 1 to 4 (A4, A5, A6 and A7) passed through a nylon filtration membrane were lower than the quantification limit. Any significant difference was not observed in contents of mouse IgG and bovine serum proteins as other impurities in the products obtained by using or not using the nylon filtration membrane (Table 5). As described above, the nylon filtration membrane gave specific removing ability for HCP also in industrial level production, and enabled production of highly-purified soluble thrombomodulin having an HCP content less than 10 ng/10,000 U of thrombomodulin.

Thrombomodulin purities based on the total proteins of the highly-purified soluble thrombomodulin products obtained in Examples 1 to 4 were measured by gel filtration liquid chromatography and ion exchange liquid chromatography. The measurement by gel filtration liquid chromatography was performed by using TOSOH TSKgel G3000SWXL (TOSOH, Japan), and a 50 mM phosphate buffer (pH 7.3) containing 0.1 M sodium sulfate under the conditions of a temperature of 40° C. and a flow rate of 0.9 mL/minute. As a result, purities of the purified products (A4, A5, A6 and A7) were all higher than 99%. Further, the measurement by ion exchange liquid chromatography was performed by using TOSOH DEAE 5PW (TOSOH, Japan) with elution using a linear gradient of from a 20 mM piperazine-hydrochloric acid buffer (pH 5.6) containing 50 mM sodium chloride to a 20 mM piperazine-hydrochloric acid buffer (pH 5.6) containing 350 mM sodium chloride over 30 minutes under the conditions of a temperature of 40° C. and a flow rate of 0.9

TABLE 4

| Purified product | HCP content (ng/10,000U) | | Mouse IgG content (ng/10,000U) | | Bovine serum protein content (ng/10,000U) | |
|---|---|---|---|---|---|---|
| | Before filtration | After filtration | Before filtration | After filtration | Before filtration | After filtration |
| Comparative Example 1 (A1) | 40.9 | <8.2 | <0.18 | <0.18 | 0.67 | 1.03 |
| Comparative Example 2 (B1) | 26.0 | <6.7 | <0.16 | <0.16 | 0.24 | <0.16 |
| Comparative Example 3 (B2) | 20.0 | 7.0 | 0.65 | 0.59 | 13.5 | 13.2 |

Test Example 5

Comparison of Purities of Thrombomodulin Purified Products Obtained with or without Use of Nylon Filtration Membrane HCP contents, mouse IgG contents, and bovine serum protein contents of the thrombomodulin purified products obtained by the industrial level production using no nylon filtration membrane (Comparative Example 1) and the indusmL/minute. As a result, the purities of the purified products (A4, A5, A6 and A7) were all higher than 99%.

Further, when molecular weights of a soluble thrombomodulin purified product prepared as described in Comparative Example 1, of which molecular weight had been already confirmed to be 64,000 by MALDI-TOF-MS, and the highly-purified soluble thrombomodulin purified products obtained in Examples 1 to 4 were compared by SDS-PAGE, the bands were detected at the same position. On the basis of this result, the molecular weight of the highly-purified soluble thrombomodulin was considered to be 64,000.

Furthermore, endotoxin contents determined by the gelling method described in Japanese Pharmacopoeia, General Test Procedures, Endotoxin Test Method <4.01> were 0.004 to 0.03 EU/10,000 U, and thus were at an extremely low level (Table 6).

TABLE 5

| Lot | | Application or non-application of filtration | HCP content (ng/10$^4$ U) | Mouse IgG content (ng/10$^4$ U) | Bovine serum protein content (ng/10$^4$ U) |
|---|---|---|---|---|---|
| Comparative Example 1 | A1 | Not used | 40.9 | <0.18 | 0.67 |
| Comparative Example 1 | A2 | Not used | 17.2 | <0.19 | 0.25 |
| Comparative Example 1 | A3 | Not used | 22.3 | <0.18 | <0.23 |
| Example 1 | A4 | Used | <8.3 | <0.21 | 1.42 |
| Example 2 | A5 | Used | <7.2 | <0.18 | 0.42 |
| Example 3 | A6 | Used | <6.2 | <0.16 | 0.71 |
| Example 4 | A7 | Used | <7.2 | <0.18 | Not measured |

TABLE 6

| Lot | | Application or non-application of filtration | Endotoxin content (EU/10$^4$ U) |
|---|---|---|---|
| Example 1 | A4 | Used | 0.0050 |
| Example 2 | A5 | Used | 0.0043 |
| Example 3 | A6 | Used | 0.0105 |
| Example 4 | A7 | Used | 0.0245 |

Test Example 6

Analysis of HCP Removed with Nylon Filtration Membrane

Highly-purified soluble thrombomodulin was prepared in the same manner as that described in Example 3, and the nylon filtration membrane used for the preparation (pore diameter: 0.4 μm+0.2 μm, membrane area: 1.8 m$^2$, SARTOLON Maxi Caps 5101307H3, Sartorius, Germany) was taken out from the housing, and cut into pieces of about 3 g each. Five of the pieces were sufficiently washed with a 20 mM phosphate buffer (pH 7.3) containing 50 mM sodium chloride, and then each piece was put into a test tube containing 40 mL of a 50 mM Tris-hydrochloric acid buffer (pH 8.0) containing 0.5% CHAPS and 200 mM sodium chloride. The proteins adsorbed on the membrane were extracted in the buffer by shaking overnight at room temperature. The entire volume of the extract was concentrated to 15 μL by using ultrafiltration membranes, Vivaspin 20 (Sartorius, Germany) and Amicon Ultra-0.5 mL (Millipore, U.S.A.). ⅓ Volume of this concentrate was subjected to SDS-PAGE (e-PAGEL5/20, Atto, Japan) and CBB staining (Quick-CBB, Wako Pure Chemical Industries, Japan). A band detected around a molecular weight of 10,000 was excised, and the gel portion was reduced with dithiothreitol, then carbamidomethylated with iodoacetamide, and subjected to enzymatic digestion with trypsin overnight. The enzymatic digestion product was subjected to LC/MS/MS, and Mascot search was performed on the basis of the obtained mass-spectrum data by using the database of NCBI to analyze the amino acid sequence of the enzymatic digestion product.

Measurement Conditions of LC/MS/MS

LC/MS/MS (measurement apparatus): DiNa-2A Multi-dimensional Autoinjector System (KYA Technologies, Japan)

MS measurement range: MS1 (m/z 400-1500), MS2 (m/z 50-1500)×3 (data dependent scanning mode)

Ionization mode: nanoESI$^+$

Column: PicoFrit Column BataBasic C18 (New Objective, U.S.A.)

Mobile Phase:

Mobile phase A: 0.1% formic acid/2% acetonitrile

Mobile phase B: 0.1% formic acid/80% acetonitrile

Gradient: 0 to 30 minutes: Mobile phase B, 5 to 40%

30 to 40 minutes: Mobile phase B, 40 to 100%

40 to 60 minutes: Mobile phase B, 100%

Flow rate: 300 mL/minute

The amino acid sequences of the fragments expected from the mass-spectrum data were as shown in (1) to (7) mentioned below, and agreed with partial sequences of histone H2B (Biochimie, 61 (1), 61-69 (1979)) shown below. This result revealed that one of constituents of HCP removed with the nylon filter was histone H2B.

(1) KESYSVYVYK (SED ID NO: 14)

(2) VLKQVHPDTGISSK (SED ID NO: 15)

(3) STITSREIQTAVR (SED ID NO: 16)

(4) EIQTAVR (SED ID NO: 17)

(5) EIQTAVRLLLPGELAK (SED ID NO: 18)

(6) LLLPGELAK (SED ID NO: 19)

(7) LLLPGELAKHAVSEGTK (SED ID NO: 20)

TABLE 7

Amino acid sequence of histone H2B (SEQ ID NO: 21)

PEPAKSAPAPKKGSKKAVTKAQKKDGKKRKRSR<u>KESYSVYVYKVLKQVHPD</u><u>TGISSK</u>AMGIMNSFVNDIFZRIAGEASRLAHYNKR<u>STITSREIQTAVRLLL</u><u>PGELAKHAVSEGTK</u>AVTKYTSSK (The boxed sequences are amino acid sequence regions of the amino acid sequence of histone H2B identical with the amino acid sequences of (1) to (7) mentioned above, which were deduced from the mass-spectrum data.)

What is claimed is:

1. A method for preparing highly-purified soluble thrombomodulin having a content of host cell-originated proteins being in a ratio of less than 10 ng of the proteins per 10,000 U of soluble thrombomodulin, which comprises the step of:
   passing a solution containing soluble thrombomodulin, which is produced by a transformant cell obtained by transfecting a host cell with a DNA containing a nucleotide sequence encoding soluble thrombomodulin, through nylon and/or polyethersulfone in the form of a membrane, non-woven fabric, or beads in order to reduce the concentration of host-cell originated proteins; and
   recovering high-purified soluble thrombomodulin that has passed through the nylon and/or polyethersulfone membrane, non-woven fabric, or beads;
   wherein the nylon and/or polyethersulfone membrane, non-woven fabric, or beads adsorbs host cell-originated proteins.

2. The preparation method according to claim 1, wherein the soluble thrombomodulin is prepared by serum-free culture of the transformant cell.

3. The method for preparing highly-purified soluble thrombomodulin according to claim 1, wherein the soluble thrombomodulin has the following properties (1) to (5);
   (1) an action of selectively binding to thrombin,
   (2) an action of promoting activation of Protein C by thrombin,
   (3) an action of extending thrombin clotting time,
   (4) an action of suppressing platelet aggregation caused by thrombin, and
   (5) anti-inflammatory action.

4. The preparation method according to claim 1, wherein the host cell is a Chinese hamster ovary cell.

5. The preparation method according to claim 1, wherein molecular weight of the soluble thrombomodulin is 50,000 to 80,000.

6. The preparation method according to claim 1, wherein the soluble thrombomodulin is a peptide containing:
   (i) the amino acid sequence of the positions 367 to 480 in the amino acid sequence of SEQ ID NO: 9 or 11, and the amino acid sequence of (ii-1) or (ii-2) mentioned below, and the peptide is soluble thrombomodulin having the following properties (1) to (5):
   (ii-1) the amino acid sequence of the positions 19 to 244 in the amino acid sequence of SEQ ID NO: 9 or 11, or
   (ii-2) the amino acid sequence of (ii-1) mentioned above, further including substitution, deletion or addition of one or more amino acid residues,
   (1) an action of selectively binding to thrombin,
   (2) an action of promoting activation of Protein C by thrombin,
   (3) an action of extending thrombin clotting time,
   (4) an action of suppressing platelet aggregation caused by thrombin, and
   (5) anti-inflammatory action.

7. The preparation method according to claim 1, wherein the soluble thrombomodulin is a peptide containing:
   (i-1) the amino acid sequence of the positions 19 to 516 in the amino acid sequence of SEQ ID NO: 9 or 11, or
   (i-2) the amino acid sequence of (i-1) mentioned above, further including substitution, deletion or addition of one or more amino acid residues, and
   the peptide is soluble thrombomodulin having the following properties (1) to (5):
   (1) an action of selectively binding to thrombin,
   (2) an action of promoting activation of Protein C by thrombin,
   (3) an action of extending thrombin clotting time,
   (4) an action of suppressing platelet aggregation caused by thrombin, and
   (5) anti-inflammatory action.

8. The preparation method according to claim 1, wherein the DNA containing a nucleotide sequence encoding soluble thrombomodulin is a DNA encoding the amino acid sequence of SEQ ID NO: 9 or 11.

9. The preparation method according to claim 1, wherein the nylon and/or polyethersulfone is in the form of a filtration membrane.

10. The preparation method according to claim 9, wherein the filtration membrane has a membrane area of 0.01 to 0.5 m$^2$ for 1 mg of the host cell-originated proteins.

11. The preparation method according to claim 1, wherein the nylon and/or polyethersulfone is nylon.

12. The preparation method according to claim 1, which is a method for preparing highly-purified soluble thrombomodulin having a content of host cell-originated proteins being in a ratio of less than 10 ng of the proteins per 10,000 U of soluble thrombomodulin, comprising:
   (a) the step of obtaining a transformant cell by transfecting a host cell with a DNA encoding the amino acid sequence of SEQ ID NO: 9 or 11,
   (b) the step of obtaining a solution containing soluble thrombomodulin by culturing the transformant cell,
   (c) the step of purifying the solution containing soluble thrombomodulin to a thrombomodulin purity of 99% or higher based on the total proteins, and
   (d) the step of passing the solution containing soluble thrombomodulin through nylon to isolate highly-purified soluble thrombomodulin having a content of host cell-originated proteins being in a ratio of less than 10 ng of the proteins per 10,000 U of soluble thrombomodulin, and
   wherein the host cell is a Chinese hamster ovary cell.

13. The method according to claim 1, wherein the highly-purified soluble thrombomodulin is industrially manufactured.

14. The method according to claim 1, wherein the highly-purified soluble thrombomodulin is used as a material for a medicament.

15. The method according to claim 1, wherein a purity of the highly-purified soluble thrombomodulin is 99% or higher based on the total proteins.

16. The method according to claim 13, wherein the soluble thrombomodulin is prepared by serum-free culture of the transformant cell.

17. The method according to claim 13, wherein the soluble thrombomodulin has the following properties (1) to (5);
  (1) an action of selectively binding to thrombin,
  (2) an action of promoting activation of Protein C by thrombin,
  (3) an action of extending thrombin clotting time,
  (4) an action of suppressing platelet aggregation caused by thrombin, and
  (5) anti-inflammatory action.

18. The method according to claim 13, wherein the host cell is a Chinese hamster ovary cell.

19. The method according to claim 13, wherein molecular weight of the soluble thrombomodulin is 50,000 to 80,000.

20. The method according to claim 13, wherein the soluble thrombomodulin is a peptide containing:
  (i) the amino acid sequence of the positions 367 to 480 in the amino acid sequence of SEQ ID NO: 9 or 11, and the amino acid sequence of (ii-1) or (ii-2) mentioned below, and the peptide is soluble thrombomodulin having the following properties (1) to (5):
  (ii-1) the amino acid sequence of the positions 19 to 244 in the amino acid sequence of SEQ ID NO: 9 or 11, or
  (ii-2) the amino acid sequence of (ii-1) mentioned above, further including substitution, deletion or addition of one or more amino acid residues,
  (1) an action of selectively binding to thrombin,
  (2) an action of promoting activation of Protein C by thrombin,
  (3) an action of extending thrombin clotting time,
  (4) an action of suppressing platelet aggregation caused by thrombin, and
  (5) anti-inflammatory action.

21. The method according to claim 13, wherein the soluble thrombomodulin is a peptide containing:
  (i-1) the amino acid sequence of the positions 19 to 516 in the amino acid sequence of SEQ ID NO: 9 or 11, or
  (i-2) the amino acid sequence of (i-1) mentioned above, further including substitution, deletion or addition of one or more amino acid residues, and the peptide is soluble thrombomodulin having the following properties (1) to (5):
  (1) an action of selectively binding to thrombin,
  (2) an action of promoting activation of Protein C by thrombin,
  (3) an action of extending thrombin clotting time,
  (4) an action of suppressing platelet aggregation caused by thrombin, and
  (5) anti-inflammatory action.

22. The method according to claim 13, wherein the DNA containing a nucleotide sequence encoding soluble thrombomodulin is a DNA encoding the amino acid sequence of SEQ ID NO: 9 or 11.

23. The method according to claim 13, wherein the nylon and/or polyethersulfone is in the form of a filtration membrane.

24. The method according to claim 23, wherein the filtration membrane has a membrane area of 0.01 to 0.5 m$^2$ for 1 mg of the host cell-originated proteins.

25. The method according to claim 13, wherein the nylon and/or polyethersulfone is nylon.

26. The method according to claim 13, which is a method for preparing highly-purified soluble thrombomodulin having a content of host cell-originated proteins being in a ratio of less than 10 ng of the proteins per 10,000 U of soluble thrombomodulin, comprising:
  (a) the step of obtaining a transformant cell by transfecting a host cell with a DNA encoding the amino acid sequence of SEQ ID NO: 9 or 11,
  (b) the step of obtaining a solution containing soluble thrombomodulin by culturing the transformant cell,
  (c) the step of purifying the solution containing soluble thrombomodulin to a thrombomodulin purity of 99% or higher based on the total proteins, and
  (d) the step of passing the solution containing soluble thrombomodulin through nylon to isolate highly-purified soluble thrombomodulin having a content of host cell-originated proteins being in a ratio of less than 10 ng of the proteins per 10,000 U of soluble thrombomodulin, and
  wherein the host cell is a Chinese hamster ovary cell.

27. The method according to claim 13, wherein the highly-purified soluble thrombomodulin is used as a material for a medicament.

28. The method according to claim 13, wherein a purity of the highly-purified soluble thrombomodulin is 99% or higher based on the total proteins.

* * * * *

SEQUENCE LISTING

<160> NUMBER OF SEQ ID NOS: 21

<210> SEQ ID NO 1
<211> LENGTH: 132
<212> TYPE: PRT
<213> ORGANISM: human

<400> SEQUENCE: 1

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
            20                  25                  30

Leu Asn Gln Thr Ser Tyr Leu Cys Val Cys Ala Glu Gly Phe Ala Pro
        35                  40                  45

Ile Pro His Glu Pro His Arg Cys Gln Met Phe Cys Asn Gln Thr Ala
    50                  55                  60

Cys Pro Ala Asp Cys Asp Pro Asn Thr Gln Ala Ser Cys Glu Cys Pro
65                  70                  75                  80

Glu Gly Tyr Ile Leu Asp Asp Gly Phe Ile Cys Thr Asp Ile Asp Glu
                85                  90                  95

Cys Glu Asn Gly Gly Phe Cys Ser Gly Val Cys His Asn Leu Pro Gly
            100                 105                 110

Thr Phe Glu Cys Ile Cys Gly Pro Asp Ser Ala Leu Val Arg His Ile
        115                 120                 125

Gly Thr Asp Cys
    130

<210> SEQ ID NO 2
<211> LENGTH: 396
<212> TYPE: DNA
<213> ORGANISM: human

<400> SEQUENCE: 2
atgcttgggg tcctggtcct tggcgcgctg gccctggccg gcctggggtt ccccgacccg     60
tgcttcagag ccaactgcga gtaccagtgc cagcccctga accaaactag ctacctctgc    120
gtctgcgccg agggcttcgc gcccattccc acgagccgc acaggtgcca gatgttttgc     180
aaccagactg cctgtccagc cgactgcgac cccaacaccc aggctagctg tgagtgccct    240
gaaggctaca tcctggacga cggtttcatc tgcacggaca tcgacgagtg cgaaaacggc    300
ggcttctgct ccggggtgtg ccacaacctc cccggtacct tcgagtgcat ctgcgggccc    360
gactcggccc ttgtccgcca cattggcacc gactgt                              396

<210> SEQ ID NO 3
<211> LENGTH: 132
<212> TYPE: PRT
<213> ORGANISM: human

<400> SEQUENCE: 3

Met Leu Gly Val Leu Val Leu Gly Ala Leu Ala Leu Ala Gly Leu Gly
1               5                   10                  15

Phe Pro Asp Pro Cys Phe Arg Ala Asn Cys Glu Tyr Gln Cys Gln Pro
            20                  25                  30

Leu Asn Gln Thr Ser Tyr Leu Cys Val Cys Ala Glu Gly Phe Ala Pro
        35                  40                  45

Ile Pro His Glu Pro His Arg Cys Gln Met Phe Cys Asn Gln Thr Ala
    50                  55                  60

```
Cys Pro Ala Asp Cys Asp Pro Asn Thr Gln Ala Ser Cys Glu Cys Pro
 65                  70                  75                  80

Glu Gly Tyr Ile Leu Asp Asp Gly Phe Ile Cys Thr Asp Ile Asp Glu
                 85                  90                  95

Cys Glu Asn Gly Gly Phe Cys Ser Gly Val Cys His Asn Leu Pro Gly
                100                 105                 110

Thr Phe Glu Cys Ile Cys Gly Pro Asp Ser Ala Leu Ala Arg His Ile
            115                 120                 125

Gly Thr Asp Cys
        130

<210> SEQ ID NO 4
<211> LENGTH: 396
<212> TYPE: DNA
<213> ORGANISM: human

<400> SEQUENCE: 4
atgcttgggg tcctggtcct tggcgcgctg gccctggccg gctgggggtt ccccgacccg    60
tgcttcagag ccaactgcga gtaccagtgc cagcccctga ccaaactag ctacctctgc   120 gtctgcgccg agggcttcgc gcccattccc cacgagccgc acaggtgcca gatgttttgc   180
aaccagactg cctgtccagc cgactgcgac cccaacaccc aggctagctg tgagtgccct   240
gaaggctaca tcctggacga cggtttcatc tgcacggaca tcgacgagtg cgaaaacggc   300
ggcttctgct ccggggtgtg ccacaacctc cccggtacct tcgagtgcat ctgcgggccc   360
gactcggccc ttgcccgcca cattggcacc gactgt                            396

<210> SEQ ID NO 5
<211> LENGTH: 480
<212> TYPE: PRT
<213> ORGANISM: human

<400> SEQUENCE: 5

Met Leu Gly Val Leu Val Leu Gly Ala Leu Ala Leu Ala Gly Leu Gly
  1               5                  10                  15

Phe Pro Ala Pro Ala Glu Pro Gln Pro Gly Gly Ser Gln Cys Val Glu
                 20                  25                  30

His Asp Cys Phe Ala Leu Tyr Pro Gly Pro Ala Thr Phe Leu Asn Ala
             35                  40                  45

Ser Gln Ile Cys Asp Gly Leu Arg Gly His Leu Met Thr Val Arg Ser
     50                  55                  60

Ser Val Ala Ala Asp Val Ile Ser Leu Leu Leu Asn Gly Asp Gly Gly
 65                  70                  75                  80

Val Gly Arg Arg Arg Leu Trp Ile Gly Leu Gln Leu Pro Pro Gly Cys
                 85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
```

```
                180              185              190
Tyr Gly Thr Pro Phe Ala Ala Arg Gly Ala Asp Phe Gln Ala Leu Pro
            195                  200                  205
Val Gly Ser Ser Ala Ala Val Ala Pro Leu Gly Leu Gln Leu Met Cys
    210                  215                  220
Thr Ala Pro Pro Gly Ala Val Gln Gly His Trp Ala Arg Glu Ala Pro
225                  230                  235                  240
Gly Ala Trp Asp Cys Ser Val Glu Asn Gly Gly Cys Glu His Ala Cys
                245                  250                  255
Asn Ala Ile Pro Gly Ala Pro Arg Cys Gln Cys Pro Ala Gly Ala Ala
            260                  265                  270
Leu Gln Ala Asp Gly Arg Ser Cys Thr Ala Ser Ala Thr Gln Ser Cys
        275                  280                  285
Asn Asp Leu Cys Glu His Phe Cys Val Pro Asn Pro Asp Gln Pro Gly
    290                  295                  300
Ser Tyr Ser Cys Met Cys Glu Thr Gly Tyr Arg Leu Ala Ala Asp Gln
305                  310                  315                  320
His Arg Cys Glu Asp Val Asp Cys Ile Leu Glu Pro Ser Pro Cys
                325                  330                  335
Pro Gln Arg Cys Val Asn Thr Gln Gly Gly Phe Glu Cys His Cys Tyr
            340                  345                  350
Pro Asn Tyr Asp Leu Val Asp Gly Glu Cys Val Glu Pro Val Asp Pro
        355                  360                  365
Cys Phe Arg Ala Asn Cys Glu Tyr Gln Cys Gln Pro Leu Asn Gln Thr
    370                  375                  380
Ser Tyr Leu Cys Val Cys Ala Glu Gly Phe Ala Pro Ile Pro His Glu
385                  390                  395                  400
Pro His Arg Cys Gln Met Phe Cys Asn Gln Thr Ala Cys Pro Ala Asp
                405                  410                  415
Cys Asp Pro Asn Thr Gln Ala Ser Cys Glu Cys Pro Glu Gly Tyr Ile
            420                  425                  430
Leu Asp Asp Gly Phe Ile Cys Thr Asp Ile Asp Glu Cys Glu Asn Gly
        435                  440                  445
Gly Phe Cys Ser Gly Val Cys His Asn Leu Pro Gly Thr Phe Glu Cys
    450                  455                  460
Ile Cys Gly Pro Asp Ser Ala Leu Val Arg His Ile Gly Thr Asp Cys
465                  470                  475                  480

<210> SEQ ID NO 6
<211> LENGTH: 1440
<212> TYPE: DNA
<213> ORGANISM: human

<400> SEQUENCE: 6
atgcttgggg tcctggtcct tggcgcgctg gccctggccg gcctgggggtt ccccgcaccc    60 gcagagccgc agccgggtgg cagccagtgc gtcgagcacg actgcttcgc gctctacccg   120
ggccccgcga ccttcctcaa tgccagtcag atctgcgacg actgcggggg ccacctaatg   180
acagtgcgct cctcggtggc tgccgatgtc atttccttgc tactgaacgg cgacggcggc   240
gttggccgcc ggcgcctctg gatcggcctg cagctgccac ccggctgcgg cgaccccaag   300
cgcctcgggc ccctgcgcgg cttccagtgg gttacgggag acaacaacac cagctatagc   360
aggtgggcac ggctcgacct caatggggct cccctctgcg gccgttgtg cgtcgctgtc   420 tccgctgctg aggccactgt gcccagcgag ccgatctggg aggagcagca gtgcgaagtg   480
```

```
aaggccgatg gcttcctctg cgagttccac ttcccagcca cctgcaggcc actggctgtg     540
gagcccggcg ccgcggctgc cgccgtctcg atcacctacg gcaccccgtt cgcggcccgc     600
ggagcggact tccaggcgct gccggtgggc agctccgccg cggtggctcc cctcggctta     660
cagctaatgt gcaccgcgcc gcccggagcg gtccaggggc actgggccag ggaggcgccg     720
ggcgcttggg actgcagcgt ggagaacggc ggctgcgagc acgcgtgcaa tgcgatccct     780
ggggctcccc gctgccagtg cccagccggc gccgccctgc aggcagacgg cgctcctgc      840 accgcatccg cgacgcagtc ctgcaacgac ctctgcgagc acttctgcgt tcccaacccc     900
gaccagccgg gctcctactc gtgcatgtgc gagaccggct accggctggc ggccgaccaa     960
caccggtgcg aggacgtgga tgactgcata ctggagccca gtccgtgtcc gcagcgctgt    1020
gtcaacacac agggtggctt cgagtgccac tgctacccta actacgacct ggtggacggc    1080
gagtgtgtgg agcccgtgga cccgtgcttc agagccaact gcgagtacca gtgccagccc    1140
ctgaaccaaa ctagctacct ctgcgtctgc gccgagggct cgcgcccat tccccacgag     1200 ccgcacaggt gccagatgtt ttgcaaccag actgcctgtc agccgactg cgaccccaac     1260 acccaggcta gctgtgagtg ccctgaaggc tacatcctgg acgacggttt catctgcacg    1320
gacatcgacg agtgcgaaaa cggcggcttc tgctccgggg tgtgccacaa cctccccggt    1380
accttcgagt gcatctgcgg gcccgactcg gcccttgtcc gccacattgg caccgactgt    1440

<210> SEQ ID NO 7
<211> LENGTH: 480
<212> TYPE: PRT
<213> ORGANISM: human

<400> SEQUENCE: 7

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Asn Gly Asp Gly Gly Val
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
                180                 185                 190

Tyr Gly Thr Pro Phe Ala Ala Arg Gly Ala Asp Phe Gln Ala Leu Pro
            195                 200                 205
```

```
Val Gly Ser Ser Ala Ala Val Ala Pro Leu Gly Leu Gln Leu Met Cys
        210                 215                 220
Thr Ala Pro Pro Gly Ala Val Gln Gly His Trp Ala Arg Glu Ala Pro
225                 230                 235                 240
Gly Ala Trp Asp Cys Ser Val Glu Asn Gly Gly Cys Glu His Ala Cys
                245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
        275                 280                 285
Asn Asp Leu Cys Glu His Phe Cys Val Pro Asn Pro Asp Gln Pro Gly
290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
        355                 360                 365
Cys Phe Arg Ala Asn Cys Glu Tyr Gln Cys Gln Pro Leu Asn Gln Thr
370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
        435                 440                 445
Gly Phe Cys Ser Gly Val Cys His Asn Leu Pro Gly Thr Phe Glu Cys
        450                 455                 460
Ile Cys Gly Pro Asp Ser Ala Leu Ala Arg His Ile Gly Thr Asp Cys
465                 470                 475                 480

<210> SEQ ID NO 8
<211> LENGTH: 1440
<212> TYPE: DNA
<213> ORGANISM: human

<400> SEQUENCE: 8
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcgg cttccagtgg gttacgggag acaacaacac cagctatagc     360
aggtgggcac ggctcgacct caatggggct ccctctgcg gcccgttgtg cgtcgctgtc     420
tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg caccccgtt cgcggcccgc     600
```

```
ggagcggact tccaggcgct gccggtgggc agctccgccg cggtggctcc cctcggctta      660
cagctaatgt gcaccgcgcc gcccggagcg gtccaggggc actgggccag ggaggcgccg      720
ggcgcttggg actgcagcgt ggagaacggc ggctgcgagc acgcgtgcaa tgcgatccct      780
ggggctcccc gctgccagtg cccagccggc gccgccctgc aggcagacgg gcgctcctgc      840
accgcatccg cgacgcagtc ctgcaacgac ctctgcgagc acttctgcgt tcccaacccc      900
gaccagccgg gctcctactc gtgcatgtgc gagaccggct accggctggc ggccgaccaa      960
caccggtgcg aggacgtgga tgactgcata ctggagccca gtccgtgtcc gcagcgctgt     1020
gtcaacacac agggtggctt cgagtgccac tgctacccta actacgacct ggtggacggc     1080
gagtgtgtgg agcccgtgga cccgtgcttc agagccaact gcgagtacca gtgccagccc     1140
ctgaaccaaa ctagctacct ctgcgtctgc gccgagggct cgcgcccat tccccacgag      1200 ccgcacaggt gccagatgtt ttgcaaccag actgcctgtc agccgactg cgaccccaac      1260 acccaggcta gctgtgagtg ccctgaaggc tacatcctgg acgacggttt catctgcacg     1320
gacatcgacg agtgcgaaaa cggcggcttc tgctccgggg tgtgccacaa cctccccggt     1380
accttcgagt gcatctgcgg gcccgactcg gcccttgccc gccacattgg caccgactgt     1440
```

<210> SEQ ID NO 9
<211> LENGTH: 516
<212> TYPE: PRT
<213> ORGANISM: human

<400> SEQUENCE: 9

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220
```

```
Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
            245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
            325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
450                 455                 460

Ile Cys Gly Pro Asp Ser Ala Leu Val Arg His Ile Gly Thr Asp Cys
465                 470                 475                 480

Asp Ser Gly Lys Val Asp Gly Gly Asp Ser Gly Ser Gly Glu Pro Pro
            485                 490                 495

Pro Ser Pro Thr Pro Gly Ser Thr Leu Thr Pro Pro Ala Val Gly Leu
        500                 505                 510

Val His Ser Gly
        515

<210> SEQ ID NO 10
<211> LENGTH: 1548
<212> TYPE: DNA
<213> ORGANISM: human

<400> SEQUENCE: 10
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcgg cttccagtgg gttacgggag acaacaacac cagctatagc     360
aggtgggcac ggctcgacct caatggggct cccctctgcg gcccgttgtg cgtcgctgtc     420
```

-continued

```
tccgctgctg aggccactgt gcccagcgag ccgatctggg aggagcagca gtgcgaagtg      480
aaggccgatg gcttcctctg cgagttccac ttcccagcca cctgcaggcc actggctgtg      540
gagcccggcg ccgcggctgc cgccgtctcg atcacctacg caccccgtt cgcggcccgc       600 ggagcggact ccaggcgct gccggtgggc agctccgccg cggtggctcc cctcggctta      660
cagctaatgt gcaccgcgcc gcccggagcg gtccaggggc actgggccag ggaggcgccg      720
ggcgcttggg actgcagcgt ggagaacggc ggctgcgagc acgcgtgcaa tgcgatccct     780
ggggctcccc gctgccagtg cccagccggc ccgccctgc aggcagacgg gcgctcctgc      840
accgcatccg cgacgcagtc ctgcaacgac ctctgcgagc acttctgcgt tcccaacccc     900
gaccagccgg gctcctactc gtgcatgtgc gagaccggct accggctggc ggccgaccaa    960
caccggtgcg aggacgtgga tgactgcata ctggagccca gtccgtgtcc gcagcgctgt    1020
gtcaacacac agggtggctt cgagtgccac tgctacccta actacgacct ggtggacggc    1080
gagtgtgtgg agcccgtgga cccgtgcttc agagccaact gcgagtacca gtgccagccc    1140
ctgaaccaaa ctagctacct ctgcgtctgc gccgagggct cgcgcccat tccccacgag     1200 ccgcacaggt gccagatgtt ttgcaaccag actgcctgtc cagccgactg cgaccccaac     1260
acccaggcta gctgtgagtg ccctgaaggc tacatcctgg acgacggtttt catctgcacg    1320 gacatcgacg agtgcgaaaa cggcggcttc tgctccgggg tgtgccacaa cctccccggt    1380
accttcgagt gcatctgcgg gcccgactcg cccttgtcc gccacattgg caccgactgt     1440
gactccggca aggtggacgg tggcgacagc ggctctggcg agcccccgcc cagcccgacg    1500
cccggctcca ccttgactcc tccggccgtg gggctcgtgc attcgggc               1548
```

<210> SEQ ID NO 11
<211> LENGTH: 516
<212> TYPE: PRT
<213> ORGANISM: human

<400> SEQUENCE: 11

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175
```

```
Pro Leu Ala Val Glu Pro Gly Ala Ala Ala Ala Val Ser Ile Thr
            180                 185                 190
Tyr Gly Thr Pro Phe Ala Ala Arg Gly Ala Asp Phe Gln Ala Leu Pro
        195                 200                 205
Val Gly Ser Ser Ala Ala Val Ala Pro Leu Gly Leu Gln Leu Met Cys
    210                 215                 220
Thr Ala Pro Pro Gly Ala Val Gln His Trp Ala Arg Glu Ala Pro
225                 230                 235                 240
Gly Ala Trp Asp Cys Ser Val Glu Asn Gly Cys Glu His Ala Cys
                245                 250                 255
Asn Ala Ile Pro Gly Ala Pro Arg Cys Gln Cys Pro Ala Gly Ala Ala
            260                 265                 270
Leu Gln Ala Asp Gly Arg Ser Cys Thr Ala Ser Ala Thr Gln Ser Cys
        275                 280                 285
Asn Asp Leu Cys Glu His Phe Cys Val Pro Asn Pro Asp Gln Pro Gly
    290                 295                 300
Ser Tyr Ser Cys Met Cys Glu Thr Gly Tyr Arg Leu Ala Ala Asp Gln
305                 310                 315                 320
His Arg Cys Glu Asp Val Asp Asp Cys Ile Leu Glu Pro Ser Pro Cys
                325                 330                 335
Pro Gln Arg Cys Val Asn Thr Gln Gly Gly Phe Glu Cys His Cys Tyr
            340                 345                 350
Pro Asn Tyr Asp Leu Val Asp Gly Glu Cys Val Glu Pro Val Asp Pro
        355                 360                 365
Cys Phe Arg Ala Asn Cys Glu Tyr Gln Cys Gln Pro Leu Asn Gln Thr
    370                 375                 380
Ser Tyr Leu Cys Val Cys Ala Glu Gly Phe Ala Pro Ile Pro His Glu
385                 390                 395                 400
Pro His Arg Cys Gln Met Phe Cys Asn Gln Thr Ala Cys Pro Ala Asp
                405                 410                 415
Cys Asp Pro Asn Thr Gln Ala Ser Cys Glu Cys Pro Glu Gly Tyr Ile
            420                 425                 430
Leu Asp Asp Gly Phe Ile Cys Thr Asp Ile Asp Glu Cys Glu Asn Gly
        435                 440                 445
Gly Phe Cys Ser Gly Val Cys His Asn Leu Pro Gly Thr Phe Glu Cys
    450                 455                 460
Ile Cys Gly Pro Asp Ser Ala Leu Ala Arg His Ile Gly Thr Asp Cys
465                 470                 475                 480
Asp Ser Gly Lys Val Asp Gly Gly Asp Ser Gly Ser Gly Glu Pro Pro
                485                 490                 495
Pro Ser Pro Thr Pro Gly Ser Thr Leu Thr Pro Pro Ala Val Gly Leu
            500                 505                 510
Val His Ser Gly
        515

<210> SEQ ID NO 12
<211> LENGTH: 1548
<212> TYPE: DNA
<213> ORGANISM: human

<400> SEQUENCE: 12
atgcttgggg tcctggtcct tggcgcgctg gccctggccg gctgggggtt ccccgcaccc      60
gcagagccgc agccgggtgg cagccagtgc gtcgagcacg actgcttcgc gctctacccg     120
ggccccgcga ccttcctcaa tgccagtcag atctgcgacg gactgcgggg ccacctaatg     180
```

```
acagtgcgct cctcggtggc tgccgatgtc atttccttgc tactgaacgg cgacggcggc      240
gttggccgcc ggcgcctctg gatcggcctg cagctgccac ccggctgcgg cgaccccaag      300
cgcctcgggc ccctgcgcgg cttccagtgg gttacgggag acaacaacac cagctatagc      360
aggtgggcac ggctcgacct caatggggct cccctctgcg gcccgttgtg cgtcgctgtc      420
tccgctgctg aggccactgt gcccagcgag ccgatctggg aggagcagca gtgcgaagtg      480
aaggccgatg gcttcctctg cgagttccac ttcccagcca cctgcaggcc actggctgtg      540
gagcccggcg ccgcggctgc cgccgtctcg atcacctacg caccccgtt cgcggcccgc       600 ggagcggact ccaggcgct gccggtgggc agctccgccg cggtggctcc cctcggctta      660
cagctaatgt gcaccgcgcc gcccggagcg gtccaggggc actgggccag ggaggcgccg      720
ggcgcttggg actgcagcgt ggagaacggc ggctgcgagc acgcgtgcaa tgcgatccct      780
ggggctcccc gctgccagtg cccagccggc gccgccctgc aggcagacgg cgcgctcctgc     840 accgcatccg cgacgcagtc ctgcaacgac ctctgcgagc acttctgcgt tcccaacccc      900
gaccagccgg gctcctactc gtgcatgtgc gagaccggct accggctggc ggccgaccaa      960
caccggtgcg aggacgtgga tgactgcata ctggagccca gtccgtgtcc gcagcgctgt     1020
gtcaacacac agggtggctt cgagtgccac tgctacccta actacgacct ggtggacggc     1080
gagtgtgtgg agcccgtgga cccgtgcttc agagccaact gcgagtacca gtgccagccc     1140
ctgaaccaaa ctagctacct ctgcgtctgc gccgagggct cgcgcccat tccccacgag     1200 ccgcacaggt gccagatgtt ttgcaaccag actgcctgtc cagccgactg cgaccccaac     1260
acccaggcta gctgtgagtg ccctgaaggc tacatcctgg acgacggttt catctgcacg     1320
gacatcgacg agtgcgaaaa cggcggcttc tgctccgggg tgtgccacaa cctcccggt     1380 accttcgagt gcatctgcgg gcccgactcg gcccttgccc gccacattgg caccgactgt     1440
gactccggca aggtgacgg tggcgacagc ggctctggcg agccccgcc cagcccgacg     1500 cccggctcca ccttgactcc tccggccgtg gggctcgtgc attcgggc                  1548

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
aatgtggcgg gcaagggccg a                                                 21

<210> SEQ ID NO 14
<211> LENGTH: 10
<212> TYPE: PRT
<213> ORGANISM: human

<400> SEQUENCE: 14

Lys Glu Ser Tyr Ser Val Tyr Val Tyr Lys
1               5                   10

<210> SEQ ID NO 15
<211> LENGTH: 14
<212> TYPE: PRT
<213> ORGANISM: human

<400> SEQUENCE: 15
```

```
Val Leu Lys Gln Val His Pro Asp Thr Gly Ile Ser Ser Lys
1               5                   10
```

<210> SEQ ID NO 16
<211> LENGTH: 13
<212> TYPE: PRT
<213> ORGANISM: human

<400> SEQUENCE: 16

```
Ser Thr Ile Thr Ser Arg Glu Ile Gln Thr Ala Val Arg
1               5                   10
```

<210> SEQ ID NO 17
<211> LENGTH: 7
<212> TYPE: PRT
<213> ORGANISM: human

<400> SEQUENCE: 17

```
Glu Ile Gln Thr Ala Val Arg
1               5
```

<210> SEQ ID NO 18
<211> LENGTH: 16
<212> TYPE: PRT
<213> ORGANISM: human

<400> SEQUENCE: 18

```
Glu Ile Gln Thr Ala Val Arg Leu Leu Leu Pro Gly Glu Leu Ala Lys
1               5                   10                  15
```

<210> SEQ ID NO 19
<211> LENGTH: 9
<212> TYPE: PRT
<213> ORGANISM: human

<400> SEQUENCE: 19

```
Leu Leu Leu Pro Gly Glu Leu Ala Lys
1               5
```

<210> SEQ ID NO 20
<211> LENGTH: 17
<212> TYPE: PRT
<213> ORGANISM: human

<400> SEQUENCE: 20

```
Leu Leu Leu Pro Gly Glu Leu Ala Lys His Ala Val Ser Glu Gly Thr
1               5                   10                  15

Lys
```

<210> SEQ ID NO 21
<211> LENGTH: 125
<212> TYPE: PRT
<213> ORGANISM: human

<400> SEQUENCE: 21

```
Pro Glu Pro Ala Lys Ser Ala Pro Ala Pro Lys Lys Gly Ser Lys Lys
1               5                   10                  15

Ala Val Thr Lys Ala Gln Lys Lys Asp Gly Lys Lys Arg Lys Arg Ser
            20                  25                  30

Arg Lys Glu Ser Tyr Ser Val Tyr Val Tyr Lys Val Leu Lys Gln Val
        35                  40                  45

His Pro Asp Thr Gly Ile Ser Ser Lys Ala Met Gly Ile Met Asn Ser
    50                  55                  60
```

```
Phe Val Asn Asp Ile Phe Glx Arg Ile Ala Gly Glu Ala Ser Arg Leu
 65                  70                  75                  80

Ala His Tyr Asn Lys Arg Ser Thr Ile Thr Ser Arg Glu Ile Gln Thr
                 85                  90                  95

Ala Val Arg Leu Leu Leu Pro Gly Glu Leu Ala Lys His Ala Val Ser
            100                 105                 110

Glu Gly Thr Lys Ala Val Thr Lys Tyr Thr Ser Ser Lys
            115                 120                 125
```